US009463237B2

(12) United States Patent
Falkner et al.

(10) Patent No.: US 9,463,237 B2
(45) Date of Patent: Oct. 11, 2016

(54) RECOMBINANT VIRAL VECTORS AND METHODS FOR INDUCING A HETEROSUBTYPIC IMMUNE RESPONSE TO INFLUENZA A VIRUSES

(75) Inventors: Falko-Günter Falkner, Orth/Donau (AT); Birgit Schafer, Vienna (AT); P. Noel Barrett, Klosterneuburg/Weidling (AT); Thomas R. Kreil, Klosterneuburg (AT); Hartmut Ehrlich, Vienna (AT); Annett Hessel, Orth/Donau (AT)

(73) Assignees: BAXALTA INCORPORATED, Bannockburn, IL (US); BAXALTA GMBH, Glattpark (Opfikon) (CH)

( * ) Notice: Subject to any disclaimer, the term of this patent is extended or adjusted under 35 U.S.C. 154(b) by 0 days.

(21) Appl. No.: 13/982,524

(22) PCT Filed: Jan. 30, 2012

(86) PCT No.: PCT/US2012/023085
§ 371 (c)(1),
(2), (4) Date: Nov. 5, 2013

(87) PCT Pub. No.: WO2012/106231
PCT Pub. Date: Aug. 9, 2012

(65) Prior Publication Data
US 2014/0050759 A1 Feb. 20, 2014

Related U.S. Application Data

(60) Provisional application No. 61/438,024, filed on Jan. 31, 2011.

(51) Int. Cl.
| | | |
|---|---|---|
| *C12N 7/01* | (2006.01) | |
| *C12N 15/863* | (2006.01) | |
| *A61K 39/145* | (2006.01) | |
| *A61K 39/285* | (2006.01) | |
| *A61K 39/12* | (2006.01) | |
| *A61K 39/00* | (2006.01) | |

(52) U.S. Cl.
CPC ............. *A61K 39/285* (2013.01); *A61K 39/12* (2013.01); *A61K 39/145* (2013.01); *A61K 2039/5256* (2013.01); *A61K 2039/70* (2013.01); *C07K 2319/00* (2013.01); *C12N 2710/24143* (2013.01); *C12N 2760/16134* (2013.01)

(58) Field of Classification Search
None
See application file for complete search history.

(56) References Cited

U.S. PATENT DOCUMENTS

| | | |
|---|---|---|
| 6,998,252 B1 | 2/2006 | Moss et al. |
| 7,015,024 B1 | 3/2006 | Moss et al. |
| 7,045,136 B1 | 5/2006 | Moss et al. |
| 7,045,313 B1 | 5/2006 | Moss et al. |

FOREIGN PATENT DOCUMENTS

| | | | | |
|---|---|---|---|---|
| WO | WO-2008/118487 A2 | 10/2008 | | |
| WO | WO-2010/056991 | 5/2010 | | |
| WO | WO 2010/117786 | * 10/2010 | ........... | A61K 39/145 |
| WO | WO-2010/117786 A1 | 10/2010 | | |

OTHER PUBLICATIONS

Bender et al (Journal of Virology 70:6418-6425, 1996).*
Steel et al (mBio1(1):e300018-10, pp. 1-9; 2010).*
Sun et al (PNAS 108:4164-4169, 2011).*
Andrew et al., Cell-mediated immune responses to influenza virus antigens expressed by vaccinia virus recombinants, Microbial Pathogenesis, 1:443-52 (1986).
Andrew et al., The roles of influenza virus haemagglutinin and nucleoprotein in protection: analysis using vaccinia virus recombinants, Scand J. Immunol., 25:21-8 (1987).
Antoine et al., Characterization of the vaccinia MVA hemagglutinin gene locus and its evaluation as an insertion site for foreign genes, Gene, 177(1-2):43-6 (1996).
Antoine et al., The complete genomic sequence of the modified vaccinia Ankara strain: comparison with other orthopoxviruses, Virology, 244(2):365-96 (1998).
Assarsson et al., Immunomic analysis of the repertoire of T-cell specificities for influenza A virus in humans, J. Virol., 82(24):12241-51 (2008).
Berthoud et al., Potent CD8+ T-cell immunogenicity in humans of a novel heterosubtypic influenza A vaccine, MVA-NP+M1, Clin. Infect. Dis., 52(1):1-7 (2011).
Bommakanti et al., Design of an HA2-based Escherichia coli expressed influenza immunogen that protects mice from pathogenic challenge, Proc. Natl. Acad. Sci. USA, 107(31):13701-6 (2010).
Bright et al., Influenza virus-like particles elicit broader immune responses than whole virion inactivated influenza virus or recombinant hemagglutinin, Vaccine, 24(19):3871-8 (2007).
Brookes et al., Safety and immunogenicity of the candidate tuberculosis vaccine MVA85A in West Africa, PLoS One, 3(8):e2921 (2008).
Carroll et al., Poxviruses as expression vectors, Curr. Opin. Biotechnol., 8(5):573-7 (1997).
Cebere et al., Phase I clinical trial safety of DNA- and modified virus Ankara-vectored human immunodeficiency virus type 1 (HIV-1) vaccines administered alone and in a prime-boost regime to healthy HIV-1-uninfected volunteers, Vaccine, 24(4):417-25 (2006).
Chakrabarti et al., Compact, synthetic, vaccinia virus early/late promoter for protein expression, Biotechniques, 23(6):1094-7 (1997).

(Continued)

*Primary Examiner* — Mary E Mosher
(74) *Attorney, Agent, or Firm* — Marshall, Gerstein & Borun LLP

(57) ABSTRACT

The present invention relates to recombinant viral vectors and methods of using the recombinant viral vectors to induce an immune response to influenza A viruses. The invention provides recombinant viral vectors based, for example, on the non-replicating modified vaccinia virus Ankara. When administered according to methods of the invention, the recombinant viral vectors are designed to be cross-protective and induce heterosubtypic immunity to influenza A viruses.

3 Claims, 11 Drawing Sheets

(56) References Cited

OTHER PUBLICATIONS

Figure 10:
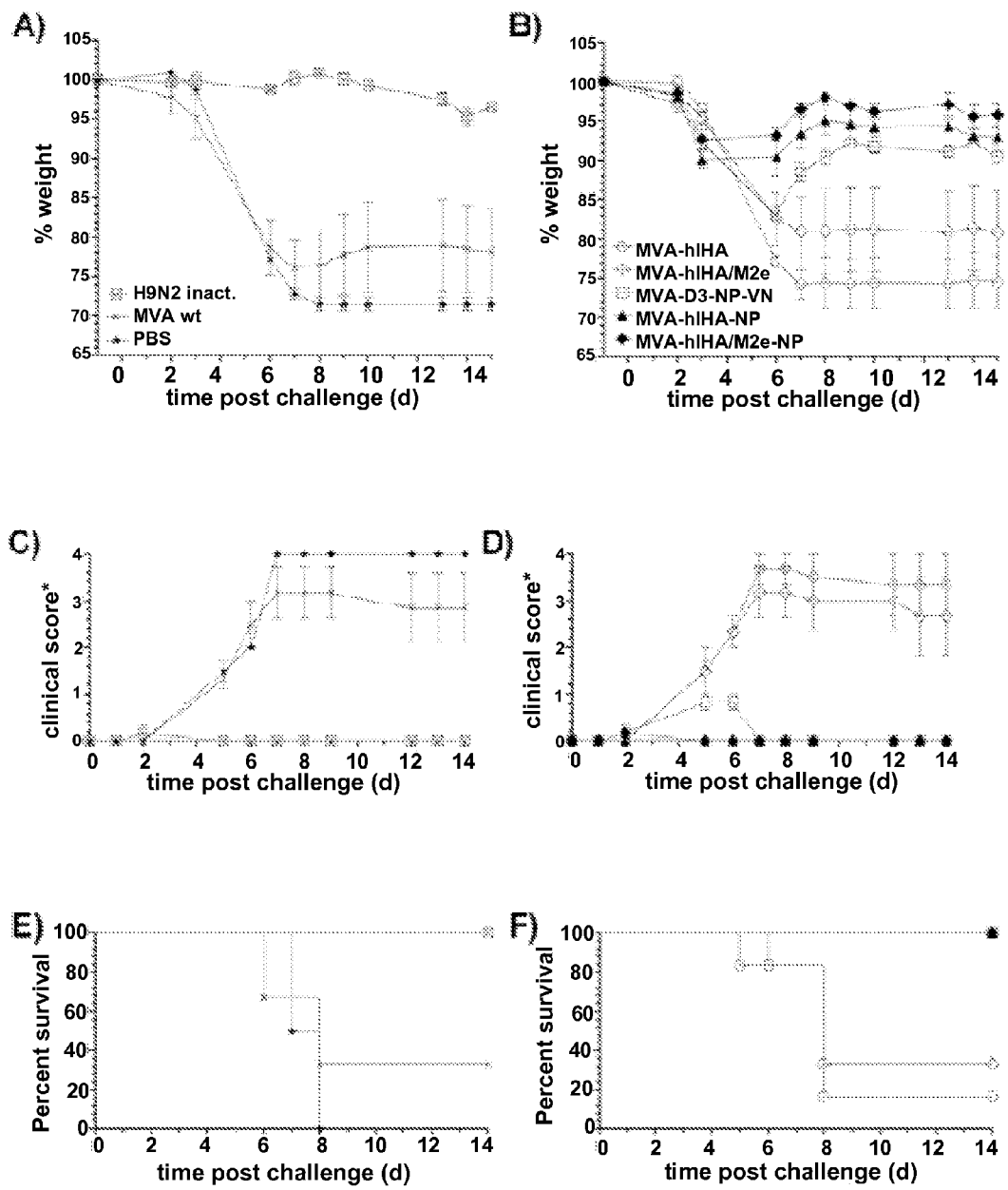

Chang et al., A single dose of DNA vaccine based on conserved H5N1 subtype proteins provides protection against lethal H5N1 challenge in mice pre-exposed to H1N1 influenza virus, Virol. J., 7:197 (2010).

Chen et al., A soluble domain of the membrane-anchoring chain of influenza virus hemagglutinin (HA2) folds in Escherichia coli into the low-pH-induced conformation, Proc. Natl. Acad. Sci. USA, 92(26):12205-9 (1995).

Chen et al., Influenza virus hemagglutinin (H3 subtype) requires palmitoylation of its cytoplasmic tail for assembly: M1 proteins of two subtypes differ in their ability to support assembly, J. Virol., 79(21):13673-84 (2005).

Chen et al., Influenza virus hemagglutinin and neuraminidase, but not the matrix protein, are required for assembly and budding of plasmid-derived virus-like particles, J. Virol., 81(13):7111-23 (2007).

De Filette et al., An influenza A vaccine based on tetrameric ectodomain of matrix protein 2, J. Biol. Chem., 283(17):11382-7 (2008).

Denis et al., Development of a universal influenza A vaccine based on the M2e peptide fused to the papaya mosaic virus (PapMV) vaccine platform, Vaccine, 26(27-28):3395-403 (2008).

Du et al., Research and development of universal influenza vaccines, Microbes and Infection, 12:280-6 (2010).

Ekiert et al., Antibody recognition of a highly conserved influenza virus epitope, Science, 324(5924):246-51 (2009).

Eliasson et al., CTA1-M2e-DD: a novel mucosal adjuvant targeted influenza vaccine, Vaccine, 26(9):1243-52 (2008).

Epstein, Prior H1N1 influenza infection and susceptibility of Cleveland Family Study participants during the H2N2 pandemic of 1957: an experiment of nature, J. Infect. Dis., 193(1):49-53 (2006).

Fan et al., Preclinical study of influenza virus a M2 peptide conjugate vaccines in mice, ferrets, and rhesus monkeys, Vaccine, 22(23-24):2993-3003 (2004).

Fiers et al., M2e-based universal influenza A vaccine, Vaccine, 27(45):6280-3 (2009).

Gomez-Puertas et al., Influenza virus matrix protein is the major driving force in virus budding, J. Virol., 74(24):11538-47 (2000).

Gomez-Puertas et al., Efficient formation of influenza virus-like particles: dependence on the expression levels of viral proteins, J. Gen. Virol., 80:1635-45 (1999).

Graham et al., A new technique for the assay of infectivity of human adenovirus 5 DNA, Virology, 52(2):456-67 (1973).

Greenbaum et al., Pre-existing immunity against swine-origin H1N1 influenza viruses in the general human population, Proc. Natl. Acad. Sci. USA, 106(48):20365-70 (2009).

Hessel et al., A pandemic influenza H1N1 live vaccine based on modified vaccinia Ankara is highly immunogenic and protects mice in active and passive immunizations, PLoS One, 5(8):e12217 (2010).

Hessel et al., Vectors based on modified vaccinia Ankara expressing influenza H5N1 hemagglutinin induce substantial cross-clade protective immunity, PLoS One, 6(1):e16247 (2011).

Hoelscher et al., Development of adenoviral-vector-based pandemic influenza vaccine against antigenically distinct human H5N1 strains in mice, Lancet, 367(9509):475-81 (2006).

Hoelscher et al., New pre-pandemic influenza vaccines: an egg- and adjuvant-independent human adenoviral vector strategy induces long-lasting protective immune responses in mice, Clin. Pharmacol. Ther., 82(6):665-71 (2007).

Holzer et al., Dominant host range selection of vaccinia recombinants by rescue of an essential gene, Virology, 249(1):160-6 (1998).

International Preliminary Report on Patentability, corresponding international application No. PCT/US2012/023085, Aug. 6, 2013.

International Search Report and Written Opinion, corresponding international application No. PCT/US2012/023085, Aug. 8, 2012.

Joseph et al., Evaluation of replication and pathogenicity of avian influenza A H7 subtype viruses in a mouse model, J. Virol., 81(19):10558-66 (2007).

Kang et al., Novel vaccines against influenza viruses, Virus Res., 162(1-2):31-8 (2011).

Kashyap et al., Combinatorial antibody libraries from survivors of the Turkish H5N1 avian influenza outbreak reveal virus neutralization strategies, Proc. Natl. Acad. Sci. USA, 105(16):5986-91 (2008).

Katz et al., Molecular correlates of influenza A H5N1 virus pathogenesis in mice, J. Virol., 74(22):10807-10 (2000).

Kistner et al., Cell culture (vero) derived whole virus (H5N1) vaccine based on wild-type strain induces cross-protective immune responses, Vaccine 25(32):6028-36 (2007).

Kreijtz et al., Cross-recognition of avian H5N1 influenza virus by human cytotoxic T-lymphocyte populations directed to human influenza A virus, J. Virol., 82(11):5161-6 (2008).

Kreijtz et al., Evaluation of a modified vaccinia virus Ankara (MVA)-based candidate pandemic influenza A/H1N1 vaccine in the ferret model, J. Gen. Virol., 91:2745-52 (2010).

Kreijtz et al., MVA-based H5N1 vaccine affords cross-clade protection in mice against influenza A/H5N1 viruses at low doses and after single immunization, PLoS One, 4(11):e7790 (2009).

Kreijtz et al., Preclinical evaluation of a modified vaccinia virus Ankara (MVA)-based vaccine against influenza A/H5N1 viruses, Vaccine, 27(45):6296-9 (2009).

Kreijtz et al., Recombinant modified vaccinia virus Ankara expressing the hemagglutinin gene confers protection against homologous and heterologous H5N1 influenza virus infections in macaques, J. Infect. Dis., 199(3):405-13 (2009).

Kreijtz et al., Recombinant modified vaccinia virus Ankara-based vaccine induces protective immunity in mice against infection with influenza virus H5N1, J. Infect. Dis., 195(11):1598-606 (2007).

Lamb et al., The proton selective ion channels of influenza A and B viruses, pp. 65-92, IN: Kawaoka (ed.), Influenza Virology: Current Topics, Caister Academic Press (2006).

Lambert et al., Influenza vaccines for the future, N. Engl. J. Med., 363(21):2036-44 (2010).

Latham et al., Formation of wild-type and chimeric influenza virus-like particles following simultaneous expression of only four structural proteins, J. Virol., 75(13):6154-65 (2001).

Lee et al., Memory T cells established by seasonal human influenza A infection cross-react with avian influenza A (H5N1) in healthy individuals, J. Clin. Invest., 118(10):3478-90 (2008).

Lu et al., A mouse model for the evaluation of pathogenesis and immunity to influenza A (H5N1) viruses isolated from humans, J. Virol., 73(7):5903-11 (1999).

Mackett et al., Vaccinia virus: a selectable eukaryotic cloning and expression vector, Proc. Natl. Acad. Sci. USA, 79(23):7415-9 (1982).

Mayr et al., Abstammung, eigenschaften and verwendung des attenuierten vaccinia-stammes MVA, Infection, 3:6-14 (1975)—Abstract in English only.

Mayrhofer et al., Nonreplicating vaccinia virus vectors expressing the H5 influenza virus hemagglutinin produced in modified Vero cells induce robust protection, J. Virol., 83(10):5192-203 (2009).

McMichael et al., Recognition of influenza A virus nucleoprotein by human cytotoxic T lymphocytes, J. Gen. Virol., 67(Pt. 4):719-26 (1986).

Mena et al., Rescue of a synthetic chloramphenicol acetyltransferase RNA into influenza viruslike particles obtained from recombinant plasmids, 70(8):5016-24 (1996).

Meyer et al., Mapping of deletions in the genome of the highly attenuated vaccinia virus MVA and their influence on virulence, J. Gen. Virol., 72(Pt. 5):1031-8 (1991).

Moss et al., Host range restricted, non-replicating vaccinia virus vectors as vaccine candidates, Adv. Exp. Med. Biol., 397:7-13 (1996).

Neirynck et al., A universal influenza A vaccine based on the extracellular domain of the M2 protein, Nat. Med., 5(10):1157-63 (1999).

(56) References Cited

OTHER PUBLICATIONS

Noton et al., Identification of the domains of the influenza A virus M1 matrix protein required for NP binding, oligomerization and incorporation into virions, J. Gen. Virol., 88:2280-90 (2007).

Okuno et al., A common neutralizing epitope conserved between the hemagglutinins of influenza A virus H1 and H2 strains, J. Virol., 67(5):2552-8 (1993).

Poon et al., Vaccinia virus-based multivalent H5N1 avian influenza vaccines adjuvanted with IL-15 confer sterile cross-clade protection in mice, J. Immunol., 182(5):3063-71 (2009).

Price et al., Single-dose mucosal immunization with a candidate universal influenza vaccine provides rapid protection from virulent H5N1, H3N2 and H1N1 viruses, PLoS One, 5(10):e13162 (2010).

Price et al., Vaccination focusing immunity on conserved antigens protects mice and ferrets against virulent H1N1 and H5N1 influenza A viruses, Vaccine, 27(47):6512-21 (2009).

Pushko et al., Influenza virus-like particles comprised of the HA, NA, and M1 proteins of H9N2 influenza virus induce protective immune responses in BALB/c mice, Vaccine, 23(50):5751-9 (2005).

Rao et al., Comparative efficacy of hemagglutinin, nucleoprotein, and matrix 2 protein gene-based vaccination against H5N1 influenza in mouse and ferret, PLoS One, 5(3):e9812 (2010).

Ricci et al., Selection of recombinant MVA by rescue of the essential D4R gene, Virol. J., 8:429 (2011).

Rimmelzwaan et al., Candidate influenza vaccines based on recombinant modified vaccinia virus Ankara, Expert Rev. Vaccines, 8(4):447-54 (2009).

Sanchez-Fauquier et al., Isolation of cross-reactive, subtype-specific monoclonal antibodies against influenza virus HA1 and HA2 hemagglutinin subunits, Arch. Virol., 94(3-4):251-65 (1987).

Scheiflinger et al., Transient marker stabilisation: a general procedure to construct marker-free recombinant vaccinia virus, Arch. Virol., 143(3):467-74 (1998).

Schotsaert et al., Universal M2 ectodomain-based influenza A vaccines: preclinical and clinical developments, Expert Rev. Vaccines, 8(4):499-508 (2009).

Slavik et al., Optimized conditions of tick-borne encephalitis virus production in vitro, Acta Virol., 27(2):97-104 (1983).

Smith et al., Synthesis and cellular location of the ten influenza polypeptides individually expressed by recombinant vaccinia viruses, Virology, 160(2):336-45 (1987).

Song et al., Protective immunity against H5N1 influenza virus by a single dose vaccination with virus-like particles, Virology, 405(1):165-75 (2010).

Steel et al., Influenza virus vaccine based on the conserved hemagglutinin stalk domain, MBio, 1(1):e00018-10 (2010).

Sui et al., Structural and functional bases for broad-spectrum neutralization of avian and human influenza A viruses, Nat. Struct. Mol. Biol., 16(3):265-73 (2009).

Throsby et al., Heterosubtypic neutralizing monoclonal antibodies cross-protective against H5N1 and H1N1 recovered from human IgM+ memory B cells, PLoS One, 3(12):e3942 (2008).

Tykodi et al., Development of modified vaccinia Ankara-5T4 as specific immunotherapy for advanced human cancer, Expert Opin. Biol. Ther., 8(12):1947-53 (2008).

Ulmer et al., Heterologous protection against influenza by injection of DNA encoding a viral protein, Science, 259(5102):1745-9 (1993).

Wu et al., Heterosubtypic protection conferred by combined vaccination with M2e peptide and split influenza vaccine, Vaccine, 27(43):6095-101 (2009).

Wyatt et al., Development of a replication-deficient recombinant vaccinia virus vaccine effective against parainfluenza virus 3 infection in an animal model, Vaccine, 14(15):1451-8 (1996).

Yewdell et al., Influenza A virus nucleoprotein is a major target antigen for cross-reactive anti-influenza A virus cytotoxic T lymphocytes, Proc. Natl. Acad. Sci. USA, 82(6):1785-9 (1985).

Zhao et al., An H5N1 M2e-based multiple antigenic peptide vaccine confers heterosubtypic protection from lethal infection with pandemic 2009 H1N1 virus, Virol. J., 7:151 (2010).

Zhao et al., An M2e-based multiple antigenic peptide vaccine protects mice from lethal challenge with divergent H5N1 influenza viruses, Virol. J., 7:9 (2010).

Zhou et al., A universal influenza A vaccine based on adenovirus expressing matrix-2 ectodomain and nucleoprotein protects mice from lethal challenge, Mol. Ther., 18(12):2182-9 (2010).

Ilyushina et al., Adaptation of pandemic H1N1 influenza viruses in mice, J. Virol., 84(17):8607-16 (2010).

\* cited by examiner

FIGURE 1

MEKIVLLFAIVSLVKSDQICIGYHANNSTEQVDTI
MEKNVTVTHAQDILEKKHNGKLCGGGGCNTKCQ
TPMGAINSSMPFHNIHPLTIGECPKYVKSNRLVLAT
GLRNSPQRERRR<u>KKR</u>GLFGAIAGFIEGGWQGMVD
GWYGYHHSNEQGSGYAADKESTQKAIDGVTNKV
NSIIDKMNTQFEAVGREFNNLERRIENLNKKMEDG
FLDVWTYNAELLVLMENERTLDFHDSNVKNLYDK
VRLQLRDNAKELGNGCFEFYHKCDNECMESVRNG
TYDYPQYSEEARLKREEISGVKLESIGIYQILSIYST
VASSLALAIMVAGLSLWMCSNGSLQCRICI

FIGURE 2

ATGGAGAAAATAGTGCTTCTTTTTGCAATAGTCAGTCT
TGTTAAAAGTGATCAGATTTGCATTGGTTACCATGCAA
ACAACTCGACAGAGCAGGTTGACACAATAATGGAAA
AGAACGTTACTGTTACACATGCCCAAGACATACTGGA
AAAGAAACACAACGGGAAGCTCTGCGGAGGAGGAGG
ATGCAACACCAAGTGTCAAACTCCAATGGGGGCGATA
AACTCTAGCATGCCATTCCACAATATACCCTCTCAC
CATTGGGGAATGCCCCAAATATGTGAAATCAAACAGA
TTAGTCCTTGCGACTGGGCTCAGAAATAGCCCTCAAA
GAGAGAGAAGAAGAAAAAGAGAGGATTATTTGGAG
CTATAGCAGGTTTTATAGAGGGAGGATGGCAGGGAAT
GGTAGATGGTTGGTATGGGTACCACCATAGCAATGAG
CAGGGGAGTGGGTACGCTGCAGACAAAGAATCCACTC
AAAAGGCAATAGATGGAGTCACCAATAAGGTCAACTC
GATCATTGACAAAATGAACACTCAGTTTGAGGCCGTT
GGAAGGGAATTTAACAACTTAGAAAGGAGAATAGAG
AATTTAAACAAGAAGATGGAAGACGGGTTCCTAGATG
TCTGGACTTATAATGCTGAACTTCTGGTTCTCATGGAA
AATGAGAGAACTCTAGACTTTCATGACTCAAATGTCA
AGAACCTTTACGACAAGGTCCGACTACAGCTTAGGGA
TAATGCAAAGGAGCTGGGTAACGGTTGTTTCGAGTTC
TATCATAAATGTGATAATGAATGTATGGAAAGTGTAA
GAAATGGAACGTATGACTACCCGCAGTATTCAGAAGA
AGCGAGACTAAAAGAGAGGAAATAAGTGGAGTAAA
ATTGGAATCAATAGGAATTTACCAAATACTGTCAATTT
ATTCTACAGTGGCGAGTTCCCTAGCACTGGCAATCAT
GGTAGCTGGTCTATCCTTATGGATGTGCTCCAATGGAT
CGTTACAATGCAGAATTTGCATTTAA

FIGURE 3

MEKIVLLFAIVSLVKS*DQICIGYHANNSTEQVDTIME*
*KNVTVTHAQDILEKKHNGKLC*GGGSLLTEVETPTRN
EWECRCSDSSDGSAGSASLLTEVETPIRNEWGCRC
NDSSDGSAGSASLLTEVETPTRNGWECKCSDSSDG
SAGSASLLTEVETPIRKGWECNCSDSSDGGG*CNTK*
*CQTPMGAINSSMPFHNIHPLTIGECPKYVKSNRLVLAT*
*GLRNSPQRERRRKKR*GLFGAIAGFIEGGWQGMVDG
WYGYHHSNEQGSGYAADKESTQKAIDGVTNKVN
SIIDKMNTQFEAVGREFNNLERRIENLNKKMEDGF
LDVWTYNAELLVLMENERTLDFHDSNVKNLYDK
VRLQLRDNAKELGNGCFEFYHKCDNECMESVRNG
TYDYPQYSEEARLKREEISGVKLESIGIYQILSIYST
VASSLALAIMVAGLSLWMCSNGSLQCRICI

FIGURE 4

```
ATGGAGAAAATAGTGCTTCTTTTTGCAATAGTCAGTCTTGTTA
AAAGTGATCAGATTTGCATTGGTTACCATGCAAACAACTCGA
CAGAGCAGGTTGACACAATAATGGAAAGAACGTTACTGTT
ACACATGCCCAAGACATACTGGAAAAGAAACACAACGGGAA
GCTCTGCGGAGGAGGAAGTCTTCTAACCGAGGTCGAAACGCC
TACCAGAAACGAATGGGAGTGCAGATGCAGCGATTCAAGTG
ATGGAAGTGCAGGATCAGCGAGTCTTCTAACCGAGGTCGAA
ACGCCTATCAGAAACGAATGGGGGTGCAGATGCAACGATTC
AAGTGATGGAAGTGCAGGATCAGCGAGTCTTCTAACCGAGGT
CGAAACGCCTACCAGAAACGGATGGGAGTGCAAATGCAGCG
ATTCAAGTGATGGAAGTGCAGGATCAGCGAGTCTTCTAACCG
AGGTCGAAACGCCTATCAGAAAGGATGGGAGTGCAACTGC
AGCGATTCAAGTGATGGAGGAGGATGCAACACCAAGTGTCA
AACTCCAATGGGGGCGATAAACTCTAGCATGCCATTCCACAA
TATACACCCTCTCACCATTGGGGAATGCCCCAAATATGTGAA
ATCAAACAGATTAGTCCTTGCGACTGGGCTCAGAAATAGCCC
TCAAAGAGAGAAGAAGAAAAAGAGAGGATTATTTGGAG
CTATAGCAGGTTTTATAGAGGGAGGATGGCAGGGAATGGTA
GATGGTTGGTATGGGTACCACCATAGCAATGAGCAGGGGAG
TGGGTACGCTGCAGACAAAGAATCCACTCAAAAGGCAATAG
ATGGAGTCACCAATAAGGTCAACTCGATCATTGACAAAATGA
ACACTCAGTTTGAGGCCGTTGGAAGGGAATTTAACAACTTAG
AAAGGAGAATAGAGAATTTAAACAAGAAGATGGAAGACGGG
TTCCTAGATGTCTGGACTTATAATGCTGAACTTCTGGTTCTCA
TGGAAAATGAGAGAACTCTAGACTTTCATGACTCAAATGTCA
AGAACCTTTACGACAAGGTCCGACTACAGCTTAGGGATAATG
CAAAGGAGCTGGGTAACGGTTGTTTCGAGTTCTATCATAAAT
GTGATAATGAATGTATGGAAAGTGTAAGAAATGGAACGTAT
GACTACCCGCAGTATTCAGAAGAAGCGAGACTAAAAAGAGA
GGAAATAAGTGGAGTAAAATTGGAATCAATAGGAATTTACC
AAATACTGTCAATTTATTCTACAGTGGCGAGTTCCCTAGCACT
GGCAATCATGGTAGCTGGTCTATCCTTATGGATGTGCTCCAA
TGGATCGTTACAATGCAGAATTTGCATTTAA
```

FIGURE 5

A)

| D3R | D4R | hIHA | D5R | MVA-hIHA
| | | hIHA/M2e | | MVA-hIHA/M2e
| | | M2 | | MVA-M2-VN
| | | PB1 | | MVA-PB1-VN
| | | M1 | | MVA-M1-VN 87 281 nt

B)

dIII left | NP | dIII right

MVA-NP-VN
142 992 nt

FIGURE 6
A
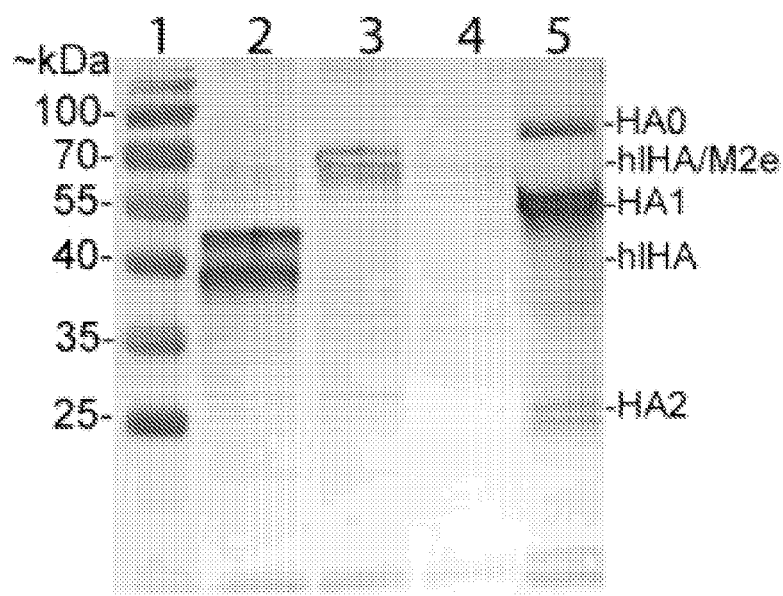
B
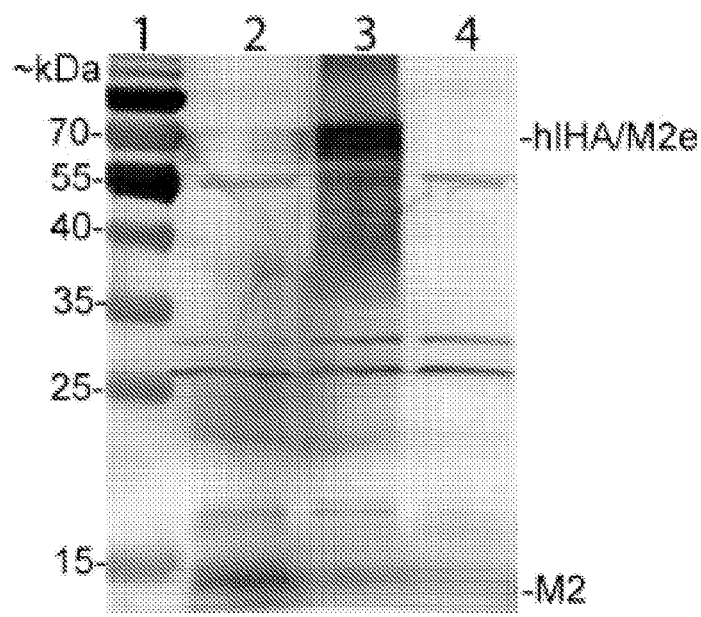

FIGURE 7

FIGURE 8
A
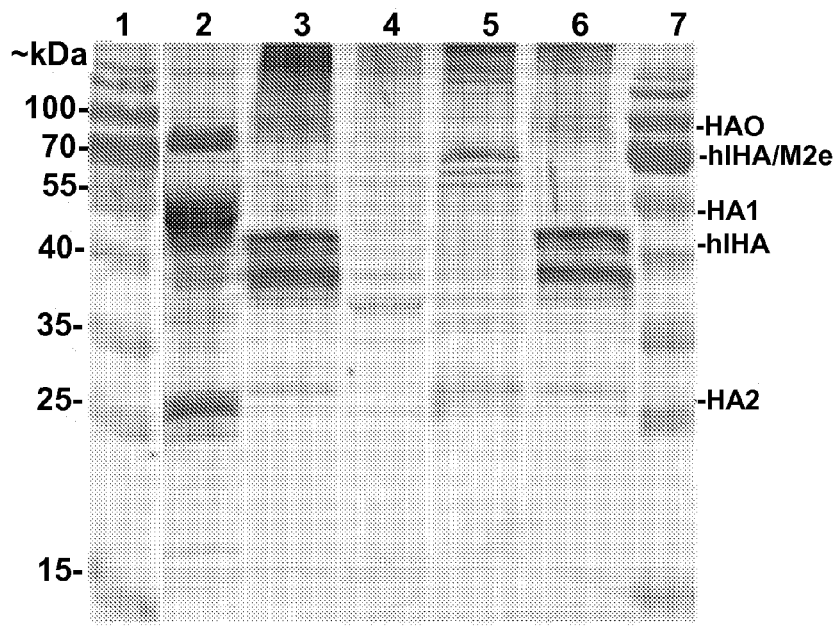
B
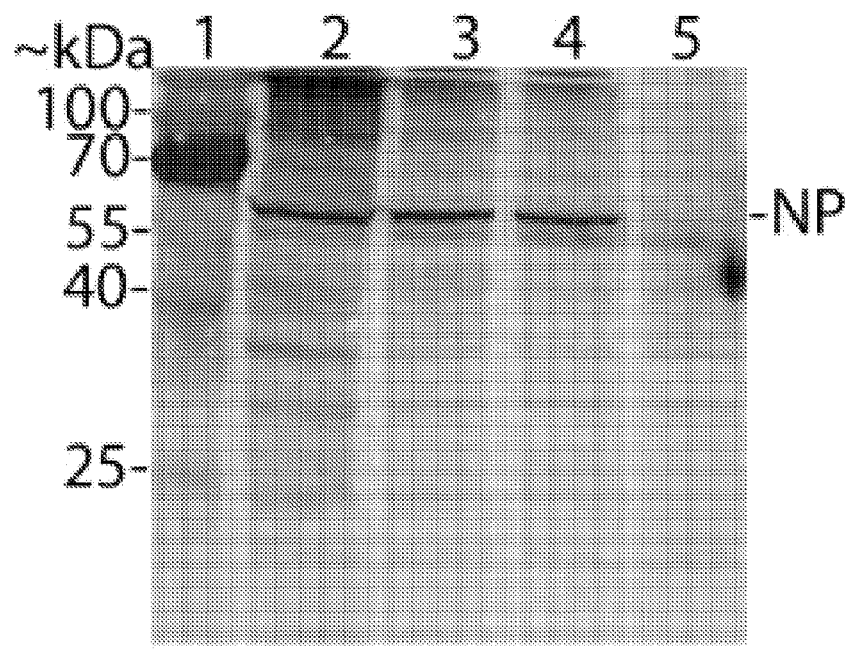

FIGURE 9

SEQUENCE LISTING

<160> NUMBER OF SEQ ID NOS: 19

<210> SEQ ID NO 1
<211> LENGTH: 1362
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: h1HA/M2e sequence
<220> FEATURE:
<221> NAME/KEY: misc_signal
<222> LOCATION: (1)..(48)
<223> OTHER INFORMATION: Signal Sequence
<220> FEATURE:
<221> NAME/KEY: misc_feature
<222> LOCATION: (49)..(174)
<223> OTHER INFORMATION: HA1 nucleotides
<220> FEATURE:
<221> NAME/KEY: misc_feature
<222> LOCATION: (175)..(183)
<223> OTHER INFORMATION: Linker
<220> FEATURE:
<221> NAME/KEY: misc_feature
<222> LOCATION: (184)..(252)
<223> OTHER INFORMATION: H5N1 M2e nucleotides
<220> FEATURE:
<221> NAME/KEY: misc_feature
<222> LOCATION: (253)..(270)
<223> OTHER INFORMATION: Linker
<220> FEATURE:
<221> NAME/KEY: misc_feature
<222> LOCATION: (271)..(339)
<223> OTHER INFORMATION: H1N1 M2e nucleotides
<220> FEATURE:
<221> NAME/KEY: misc_feature
<222> LOCATION: (340)..(357)
<223> OTHER INFORMATION: Linker
<220> FEATURE:
<221> NAME/KEY: misc_feature
<222> LOCATION: (358)..(426)
<223> OTHER INFORMATION: H9N2 M2e nucleotides
<220> FEATURE:
<221> NAME/KEY: misc_feature
<222> LOCATION: (427)..(444)
<223> OTHER INFORMATION: Linker
<220> FEATURE:
<221> NAME/KEY: misc_feature
<222> LOCATION: (445)..(513)
<223> OTHER INFORMATION: H7N2 M2e nucleotides
<220> FEATURE:
<221> NAME/KEY: misc_feature
<222> LOCATION: (514)..(522)
<223> OTHER INFORMATION: Linker
<220> FEATURE:
<221> NAME/KEY: misc_feature
<222> LOCATION: (523)..(684)
<223> OTHER INFORMATION: HA1 nucleotides
<220> FEATURE:
<221> NAME/KEY: misc_feature
<222> LOCATION: (685)..(1362)
<223> OTHER INFORMATION: HA2 nucleotides

<400> SEQUENCE: 1

| | |
|---|---|
| atggagaaaa tagtgcttct ttttgcaata gtcagtcttg ttaaaagtga tcagatttgc | 60 |
| attggttacc atgcaaacaa ctcgacagag caggttgaca caataatgga aaagaacgtt | 120 |
| actgttacac atgcccaaga catactggaa aagaaacaca cgggaagct ctgcggagga | 180 |
| ggaagtcttc taaccgaggt cgaaacgcct accagaaacg aatgggagtg cagatgcagc | 240 |
| gattcaagtg atggaagtgc aggatcagcg agtcttctaa ccgaggtcga acgcctatc | 300 |
| agaaacgaat gggggtgcag atgcaacgat tcaagtgatg gaagtgcagg atcagcgagt | 360 |
| cttctaaccg aggtcgaaac gcctaccaga aacggatggg agtgcaaatg cagcgattca | 420 |
| agtgatggaa gtgcaggatc agcgagtctt ctaaccgagg tcgaaacgcc tatcagaaaa | 480 |
| ggatgggagt gcaactgcag cgattcaagt gatggaggag gatgcaacac caagtgtcaa | 540 |
| actccaatgg gggcgataaa ctctagcatg ccattccaca atatacaccc tctcaccatt | 600 |
| ggggaatgcc ccaaatatgt gaaatcaaac agattagtcc ttgcgactgg gctcagaaat | 660 |
| agccctcaaa gagagagaag aagaaaaag agaggattat ttggagctat agcaggtttt | 720 |
| atagagggag gatggcaggg aatggtagat ggttggtatg gtaccacca tagcaatgag | 780 |
| caggggagtg ggtacgctgc agacaaagaa tccactcaaa aggcaataga tggagtcacc | 840 |
| aataaggtca actcgatcat tgacaaaatg aacactcagt tgaggccgt tggaagggaa | 900 |
| tttaacaact agaaaggag aatagagaat ttaaacaaga agatggaaga cgggttccta | 960 |
| gatgtctgga cttataatgc tgaacttctg gttctcatgg aaaatgagag aactctagac | 1020 |
| tttcatgact caaatgtcaa gaaccttac gacaaggtcc gactacagct tagggataat | 1080 |
| gcaaaggagc tgggtaacgg ttgtttcgag ttctatcata atgtgataa tgaatgtatg | 1140 |
| gaaagtgtaa gaaatggaac gtatgactac ccgcagtatt cagaagaagc gagactaaaa | 1200 |
| agagaggaaa taagtggagt aaaattggaa tcaataggaa tttaccaaat actgtcaatt | 1260 |
| tattctacag tggcgagttc cctagcactg gcaatcatgg tagctggtct atccttatgg | 1320 |
| atgtgctcca atggatcgtt acaatgcaga atttgcattt aa | 1362 |

<210> SEQ ID NO 2
<211> LENGTH: 453
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: hlHA/M2e sequence
<220> FEATURE:
<221> NAME/KEY: SIGNAL
<222> LOCATION: (1)..(16)
<223> OTHER INFORMATION: Signal sequence
<220> FEATURE:
<221> NAME/KEY: MISC_FEATURE
<222> LOCATION: (17)..(58)
<223> OTHER INFORMATION: HA1 residues
<220> FEATURE:
<221> NAME/KEY: MISC_FEATURE
<222> LOCATION: (59)..(61)
<223> OTHER INFORMATION: Linker
<220> FEATURE:
<221> NAME/KEY: MISC_FEATURE
<222> LOCATION: (62)..(84)
<223> OTHER INFORMATION: H5N1 M2e residues
<220> FEATURE:
<221> NAME/KEY: MISC_FEATURE
<222> LOCATION: (85)..(90)
<223> OTHER INFORMATION: Linker
<220> FEATURE:
<221> NAME/KEY: MISC_FEATURE
<222> LOCATION: (91)..(113)

<223> OTHER INFORMATION: H1N1 M2e residues
<220> FEATURE:
<221> NAME/KEY: MISC_FEATURE
<222> LOCAT

```
            225                 230                 235                 240
        Ile Glu Gly Gly Trp Gln Gly Met Val Asp Gly Trp Tyr Gly Tyr His
                        245                 250                 255

His Ser Asn Glu Gln Gly Ser Gly Tyr Ala Ala Asp Lys Glu Ser Thr
                        260                 265                 270

Gln Lys Ala Ile Asp Gly Val Thr Asn Lys Val Asn Ser Ile Ile Asp
                        275                 280                 285

Lys Met Asn Thr Gln Phe Glu Ala Val Gly Arg Glu Phe Asn Asn Leu
                        290                 295                 300

Glu Arg Arg Ile Glu Asn Leu Asn Lys Lys Met Glu Asp Gly Phe Leu
        305                 310                 315                 320

Asp Val Trp Thr Tyr Asn Ala Glu Leu Leu Val Leu Met Glu Asn Glu
                        325                 330                 335

Arg Thr Leu Asp Phe His Asp Ser Asn Val Lys Asn Leu Tyr Asp Lys
                        340                 345                 350

Val Arg Leu Gln Leu Arg Asp Asn Ala Lys Glu Leu Gly Asn Gly Cys
                        355                 360                 365

Phe Glu Phe Tyr His Lys Cys Asp Asn Glu Cys Met Glu Ser Val Arg
                        370                 375                 380

Asn Gly Thr Tyr Asp Tyr Pro Gln Tyr Ser Glu Glu Ala Arg Leu Lys
        385                 390                 395                 400

Arg Glu Glu Ile Ser Gly Val Lys Leu Glu Ser Ile Gly Ile Tyr Gln
                        405                 410                 415

Ile Leu Ser Ile Tyr Ser Thr Val Ala Ser Ser Leu Ala Leu Ala Ile
                        420                 425                 430

Met Val Ala Gly Leu Ser Leu Trp Met Cys Ser Asn Gly Ser Leu Gln
                        435                 440                 445

Cys Arg Ile Cys Ile
                        450

<210> SEQ ID NO 3
<211> LENGTH: 568
<212> TYPE: PRT
<213> ORGANISM: Influenza A virus
<220> FEATURE:
<221> NAME/KEY: MISC_FEATURE
<223> OTHER INFORMATION: VN/1203 HA sequence

<400> SEQUENCE: 3

Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
                20                  25                  30

Asp Thr Ile Met Glu Lys Asn Val Thr Val Thr His Ala Gln Asp Ile
            35                  40                  45

Leu Glu Lys Lys His Asn Gly Lys Leu Cys Asp Leu Asp Gly Val Lys
        50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Val Asn Asp Leu Cys Tyr Pro Gly Asp Phe Asn
                100                 105                 110

Asp Tyr Glu Glu Leu Lys His Leu Leu Ser Arg Ile Asn His Phe Glu
            115                 120                 125
```

```
Lys Ile Gln Ile Ile Pro Lys Ser Ser Trp Ser Ser His Glu Ala Ser
    130                 135                 140

Leu Gly Val Ser Ser Ala Cys Pro Tyr Gln Gly Lys Ser Ser Phe Phe
145                 150                 155                 160

Arg Asn Val Val Trp Leu Ile Lys Lys Asn Ser Thr Tyr Pro Thr Ile
                165                 170                 175

Lys Arg Ser Tyr Asn Asn Thr Asn Gln Glu Asp Leu Leu Val Leu Trp
            180                 185                 190

Gly Ile His His Pro Asn Asp Ala Ala Glu Gln Thr Lys Leu Tyr Gln
        195                 200                 205

Asn Pro Thr Thr Tyr Ile Ser Val Gly Thr Ser Thr Leu Asn Gln Arg
210                 215                 220

Leu Val Pro Arg Ile Ala Thr Arg Ser Lys Val Asn Gly Gln Ser Gly
225                 230                 235                 240

Arg Met Glu Phe Phe Trp Thr Ile Leu Lys Pro Asn Asp Ala Ile Asn
                245                 250                 255

Phe Glu Ser Asn Gly Asn Phe Ile Ala Pro Glu Tyr Ala Tyr Lys Ile
            260                 265                 270

Val Lys Lys Gly Asp Ser Thr Ile Met Lys Ser Glu Leu Glu Tyr Gly
        275                 280                 285

Asn Cys Asn Thr Lys Cys Gln Thr Pro Met Gly Ala Ile Asn Ser Ser
290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
        370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Val Arg Asn Gly Thr Tyr Asp Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Ile Tyr Gln Ile Leu Ser Ile Tyr Ser Thr Val Ala Ser Ser Leu Ala
530                 535                 540

Leu Ala Ile Met Val Ala Gly Leu Ser Leu Trp Met Cys Ser Asn Gly
```

```
                545                 550                 555                 560

Ser Leu Gln Cys Arg Ile Cys Ile
                565

<210> SEQ ID NO 4
<211> LENGTH: 3
<212> TYPE: PRT
<213> ORGANISM: Artificial Sequence
<220> FEATURE:
<223> OTHER INFORMATION: Synthetic linker

<400> SEQUENCE: 4

Gly Gly Gly
1

<210> SEQ ID NO 5
<211> LENGTH: 23
<212> TYPE: PRT
<213> ORGANISM: Influenza A virus
<220> FEATURE:
<221> NAME/KEY: MISC_FEATURE
<223> OTHER INFORMATION: H5N1 M2e sequence

<400> SEQUENCE: 5

Ser Leu Leu Thr Glu Val Glu Thr Pro Thr Arg Asn Glu Trp Glu Cys
1               5                   10                  15

Arg Cys Ser Asp Ser Ser Asp
            20

<210> SEQ ID NO 6
<211> LENGTH: 23
<212> TYPE: PRT
<213> ORGANISM: Influenza A virus
<220> FEATURE:
<221> NAME/KEY: MISC_FEATURE
<223> OTHER INFORMATION: H1N1 M2e sequence

<400> SEQUENCE: 6

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 7
<211> LENGTH: 23
<212> TYPE: PRT
<213> ORGANISM: Influenza A virus
<220> FEATURE:
<221> NAME/KEY: MISC_FEATURE
<223> OTHER INFORMATION: H9N2 M2e sequence

<400> SEQUENCE: 7

Ser Leu Leu Thr Glu Val Glu Thr Pro Thr Arg Asn Gly Trp Glu Cys
1               5                   10                  15

Lys Cys Ser Asp Ser Ser Asp
            20

<210> SEQ ID NO 8
<211> LENGTH: 23
<212> TYPE: PRT
<213> ORGANISM: Influenza A virus
<220> FEATURE:
<221> NAME/KEY: MISC_FEATURE
<223> OTHER INFORMATION: H7N2 M2e sequence

<400> SEQUENCE: 8
```

```
Ser Leu Leu Thr Glu Val Glu Thr Pro Ile Arg Lys Gly Trp Glu Cys
1               5                   10                  15

Asn Cys Ser Asp Ser Ser Asp
            20

<210> SEQ ID NO 9
<211> LENGTH: 6
<212> TYPE: PRT
<213> ORGANISM: Artificial Sequence
<220> FEATURE:
<223> OTHER INFORMATION: Synthetic linker

<400> SEQUENCE: 9

Gly Ser Ala Gly Ser Ala
1               5

<210> SEQ ID NO 10
<211> LENGTH: 986
<212> TYPE: DNA
<213> ORGANISM: Influenza A virus
<220> FEATURE:
<221> NAME/KEY: misc_feature
<223> OTHER INFORMATION: M1 sequence

<400> SEQUENCE: 10
atgagtcttc taaccgaggt cgaaacgtac gttctctcta tcatcccgtc aggccccctc     60
aaagccgaga tcgcacagaa acttgaagat gtctttgcag gaaagaacac cgatctcgag    120
gctctcatgg agtggctaaa gacaagacca atcctgtcac ctctgactaa agggattttg    180
ggatttgtat tcacgctcac cgtgcccagt gagcgaggac tgcagcgtag acgctttgtc    240
cagaatgccc taaatggaaa tggagatcca aataatatgg atagggcagt taagctatat    300
aagaagctga aaagagaaat aacattccat ggggctaagg aggtcgcact cagctactca    360
accggtgcac ttgccagttg catgggtctc atatacaaca ggatgggaac ggtgactacg    420
gaagtggctt ttggcctagt gtgtgccact tgtgagcaga ttgcagattc acagcatcgg    480
tctcacagac agatggcaac tatcaccaac ccactaatca gacatgagaa cagaatggtg    540
ctggccagca ctacagctaa ggctatggag cagatggcgg gatcaagtga gcaggcagcg    600
gaagccatgg agatcgctaa tcaggctagg cagatggtgc aggcaatgag gacaattggg    660
actcatccta actctagtgc tggtctgaga gataatcttc ttgaaaattt gcaggcctac    720
cagaaacgaa tgggagtgca gatgcagcga ttcaagtgat cctattgttg ttgccgcaaa    780
tatcattggg atcttgcact tgatattgtg gattcttgat cgtctttttct tcaaatgcat    840 ttatcgtcgc cttaaatacg gtttgaaaag agggcctgct acggcagggg tacctgagtc    900
tatgagggaa gagtaccggc aggaacagca gagtgctgtg gatgttgacg atggtcattt    960
tgtcaacata gaattggagt aaaaaa                                         986

<210> SEQ ID NO 11
<211> LENGTH: 252
<212> TYPE: PRT
<213> ORGANISM: Influenza A virus
<220> FEATURE:
<221> NAME/KEY: MISC_FEATURE
<223> OTHER INFORMATION: M1 sequence

<400> SEQUENCE: 11

Met Ser Leu Leu Thr Glu Val Glu Thr Tyr Val Leu Ser Ile Ile Pro
1               5                   10                  15
```

```
Ser Gly Pro Leu Lys Ala Glu Ile Ala Gln Lys Leu Glu Asp Val Phe
             20                  25                  30

Ala Gly Lys Asn Thr Asp Leu Glu Ala Leu Met Glu Trp Leu Lys Thr
         35                  40                  45

Arg Pro Ile Leu Ser Pro Leu Thr Lys Gly Ile Leu Gly Phe Val Phe
     50                  55                  60

Thr Leu Thr Val Pro Ser Glu Arg Gly Leu Gln Arg Arg Arg Phe Val
 65                  70                  75                  80

Gln Asn Ala Leu Asn Gly Asn Gly Asp Pro Asn Asn Met Asp Arg Ala
                 85                  90                  95

Val Lys Leu Tyr Lys Lys Leu Lys Arg Glu Ile Thr Phe His Gly Ala
            100                 105                 110

Lys Glu Val Ala Leu Ser Tyr Ser Thr Gly Ala Leu Ala Ser Cys Met
        115                 120                 125

Gly Leu Ile Tyr Asn Arg Met Gly Thr Val Thr Thr Glu Val Ala Phe
    130                 135                 140

Gly Leu Val Cys Ala Thr Cys Glu Gln Ile Ala Asp Ser Gln His Arg
145                 150                 155                 160

Ser His Arg Gln Met Ala Thr Ile Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Ile Ala Asn Gln
        195                 200                 205

Ala Arg Gln Met Val Gln Ala Met Arg Thr Ile Gly Thr His Pro Asn
    210                 215                 220

Ser Ser Ala Gly Leu Arg Asp Asn Leu Leu Glu Asn Leu Gln Ala Tyr
225                 230                 235                 240

Gln Lys Arg Met Gly Val Gln Met Gln Arg Phe Lys
                245                 250

<210> SEQ ID NO 12
<211> LENGTH: 1507
<212> TYPE: DNA
<213> ORGANISM: Influenza A virus
<220> FEATURE:
<221> NAME/KEY: misc_feature
<223> OTHER INFORMATION: NP sequence

<400> SEQUENCE: 12
atggcgtctc aaggcaccaa acgatcttat gaacagatgg aaactggtgg ggaacgccag      60
aatgctactg agatcagggc atctgttgga agaatggtta gtggcattgg gaggttctac     120
atacagatgt gcacagaact caaactcagt gactatgaag ggaggctgat ccagaacagc     180
ataacaatag agagaatggt actctctgca tttgatgaaa gaaggaacag atacctggaa     240
gaacacccca gtgcgggaaa ggacccgaag aagactggag tccaattta tcggaggaga     300 gacgggaaat gggtgagaga gctaattctg tacgacaaag aggagatcag gaggatttgg     360
cgtcaagcga acaatggaga ggacgcaact gctggtctta cccacctgat gatatggcat     420
tccaatctaa atgatgccac atatcagaga acgagagctc tcgtgcgtac tggaatggac     480
ccaaggatgt gctctctgat gcaagggtca actctcccga ggagatctgg agctgccggt     540
gcagcagtaa agggggtagg acaatggtg atggagctga ttcggatgat aaaacgaggg     600
atcaacgacc ggaattctg gagagggcgaa aatggaagaa gaacaaggat tgcatatgag     660
agaatgtgca acatcctcaa aggaaaattc caaacagcag cacaaagagc aatgatggat     720
```

```
caagtgcgag agagcagaaa tcctgggaat gctgaaattg aagatctcat ttttctggca    780
cggtctgcac tcatcctgag aggatcagtg gcccataagt cctgcttgcc tgcttgtgtg    840
tacggacttg cagtggccag tggatatgac tttgagagag aagggtactc tctggttgga    900
atagatcctt tccgcctgct tcaaaacagc caggtcttta gtctcattag accaaatgag    960
aatccagcac ataagagtca attagtgtgg atggcatgcc actctgcagc atttgaggac   1020
cttagagtct caagtttcat cagagggaca agagtggtcc caagaggaca gctatccacc   1080
agaggggttc aaattgcttc aaatgagaac atggaggcaa tggactccaa cactcttgaa   1140
ctgagaagca gatattgggc tataagaacc agaagcggag aaacaccaa ccagcagagg    1200 gcatctgcag acagatcag cgttcagccc actttctcgg tccagagaaa ccttcccttc     1260
gaaagagcga ccattatggc agcatttaca ggaaatactg agggcagaac gtctgacatg   1320
aggactgaaa tcataagaat gatggaaagt gccagaccag aagatgtgtc attccagggg   1380
cggggagtct tcgagctctc ggacgaaaag gcaacgaacc cgatcgtgcc ttcctttgac   1440
atgaataatg aaggatctta tttcttcgga gacaatgcag aggagtatga caattaaaga   1500
aaaatac                                                            1507

<210> SEQ ID NO 13
<211> LENGTH: 498
<212> TYPE: PRT
<213> ORGANISM: Influenza A virus
<220> FEATURE:
<221> NAME/KEY: MISC_FEATURE
<223> OTHER INFORMATION: NP sequence

<400> SEQUENCE: 13
```

Met Ala Ser Gln Gly Thr Lys Arg Ser Tyr Glu Gln Met Glu Thr Gly
1               5                   10                  15

Gly Glu Arg Gln Asn Ala Thr Glu Ile Arg Ala Ser Val Gly Arg Met
            20                  25                  30

Val Ser Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Ile Thr Ile Glu
    50                  55                  60

Arg Met Val Leu Ser Ala Phe Asp Glu Arg Arg Asn Arg Tyr Leu Glu
65                  70                  75                  80

Glu His Pro Ser Ala Gly Lys Asp Pro Lys Lys Thr Gly Gly Pro Ile
                85                  90                  95

Tyr Arg Arg Arg Asp Gly Lys Trp Val Arg Glu Leu Ile Leu Tyr Asp
            100                 105                 110

Lys Glu Glu Ile Arg Arg Ile Trp Arg Gln Ala Asn Asn Gly Glu Asp
        115                 120                 125

Ala Thr Ala Gly Leu Thr His Leu Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Arg Thr Arg Ile Ala Tyr Glu Arg Met Cys Asn
            210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Leu Ala Val Ala Ser Gly
        275                 280                 285

Tyr Asp Phe Glu Arg Glu Gly Tyr Ser Leu Val Gly Ile Asp Pro Phe
290                 295                 300

Arg Leu Leu Gln Asn Ser Gln Val Phe Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Ser Ser Phe Ile Arg Gly Thr Arg Val
            340                 345                 350

Val Pro Arg Gly Gln Leu Ser Thr Arg Gly Val Gln Ile Ala Ser Asn
        355                 360                 365

Glu Asn Met Glu Ala Met Asp Ser Asn Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn

<210> SEQ ID NO 14
<211> LENGTH: 1026
<212> TYPE: DNA
<213> ORGANISM: Artificial Sequence
<220> FEATURE:
<223> OTHER INFORMATION: Synthetic nucleotide
<220> FEATURE:
<221> NAME/KEY: misc_feature
<223> OTHER INFORMATION: h1HA sequence
<220> FEATURE:
<221> NAME/KEY: misc_signal
<222> LOCATION: (1)..(48)
<223> OTHER INFORMATION: Signal sequence
<220> FEATURE:
<221> NAME/KEY: misc_feature
<222> LOCATION: (49)..(174)
<223> OTHER INFORMATION: HA1 nucleotides
<220> FEATURE:
<221> NAME/KEY: misc_feature
<222> LOCATION: (175)..(186)
<223> OTHER INFORMATION: Linker
<220> FEATURE:

<221> NAME/KEY: misc_feature
<222> LOCATION: (187)..(348)
<223> OTHER INFORMATION: HA1 nucleotides
<220> FEATURE:
<221> NAME/KEY: misc_feature
<222> LOCATION: (349)..(1026)
<223> OTHER INFORMATION: HA2 stalk region

<400> SEQUENCE: 14

```
atggagaaaa tagtgcttct ttttgcaata gtcagtcttg ttaaaagtga tcagatttgc      60
attggttacc atgcaaacaa ctcgacagag caggttgaca caataatgga aaagaacgtt     120
actgttacac atgcccaaga catactggaa aagaaacaca acgggaagct ctgcggagga     180
ggaggatgca acaccaagtg tcaaactcca atgggggcga taaactctag catgccattc     240
cacaatatac accctctcac cattggggaa tgccccaaat atgtgaaatc aaacagatta     300
gtccttgcga ctgggctcag aaatagccct caaagagaga aagaagaaa aagagagga     360
ttatttggag ctatagcagg ttttatagag ggaggatggc agggaatggt agatggttgg     420
tatgggtacc accatagcaa tgagcagggg agtgggtacg ctgcagacaa agaatccact     480
caaaaggcaa tagatggagt caccaataag gtcaactcga tcattgacaa aatgaacact     540
cagtttgagg ccgttggaag ggaatttaac aacttagaaa ggagaataga gaatttaaac     600
aagaagatgg aagacgggtt cctagatgtc tggacttata atgctgaact tctggttctc     660
atggaaaatg agagaactct agactttcat gactcaaatg tcaagaacct ttacgacaag     720
gtccgactac agcttaggga taatgcaaag gagctgggta acggttgttt cgagttctat     780
cataaatgtg ataatgaatg tatggaaagt gtaagaaatg gaacgtatga ctacccgcag     840
tattcagaag aagcgagact aaaaagagag gaaataagtg gagtaaaatt ggaatcaata     900
ggaatttacc aaatactgtc aatttattct acagtggcga gttccctagc actggcaatc     960
atggtagctg gtctatcctt atggatgtgc tccaatggat cgttacaatg cagaatttgc    1020
atttaa                                                              1026
```

<210> SEQ ID NO 15
<211> LENGTH: 341
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: hlHA sequence
<220> FEATURE:
<221> NAME/KEY: SIGNAL
<222> LOCATION: (1)..(16)
<223> OTHER INFORMATION: Signal sequence
<220> FEATURE:
<221> NAME/KEY: MISC_FEATURE
<222> LOCATION: (17)..(58)
<223> OTHER INFORMATION: HA1 residues
<220> FEATURE:
<221> NAME/KEY: MISC_FEATURE
<222> LOCATION: (59)..(62)
<223> OTHER INFORMATION: Linker
<220> FEATURE:
<221> NAME/KEY: MISC_FEATURE
<222> LOCATION: (63)..(116)
<223> OTHER INFORMATION: HA1 residues
<220> FEATURE:
<221> NAME/KEY: SITE
<222> LOCATION: (112)..(119)
<223> OTHER INFORMATION: Polybasic cleavage site
<220> FEATURE:
<221> NAME/KEY: MISC_FEATURE
<222> LOCATION: (117)..(341)

-continued

<223> OTHER INFORMATION: HA2 residues

<400> SEQUENCE: 15

```
Met Glu Lys Ile Val Leu Leu Phe Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Lys His Asn Gly Lys Leu Cys Gly Gly Gly Gly Cys Asn
    50                  55                  60

Thr Lys Cys Gln Thr Pro Met Gly Ala Ile Asn Ser Ser Met Pro Phe
65                  70                  75                  80

His Asn Ile His Pro Leu Thr Ile Gly Glu Cys Pro Lys Tyr Val Lys
                85                  90                  95

Ser Asn Arg Leu Val Leu Ala Thr Gly Leu Arg Asn Ser Pro Gln Arg
            100                 105                 110

Glu Arg Arg Arg Lys Lys Arg Gly Leu Phe Gly Ala Ile Ala Gly Phe
        115                 120                 125

Ile Glu Gly Gly Trp Gln Gly Met Val Asp Gly Trp Tyr Gly Tyr His
    130                 135                 140

His Ser Asn Glu Gln Gly Ser Gly Tyr Ala Ala Asp Lys Glu Ser Thr
145                 150                 155                 160

Gln Lys Ala Ile Asp Gly Val Thr Asn Lys Val Asn Ser Ile Ile Asp
                165                 170                 175

Lys Met Asn Thr Gln Phe Glu Ala Val Gly Arg Glu Phe Asn Asn Leu
            180                 185                 190

Glu Arg Arg Ile Glu Asn Leu Asn Lys Lys Met Glu Asp Gly Phe Leu
        195                 200                 205

Asp Val Trp Thr Tyr Asn Ala Glu Leu Leu Val Leu Met Glu Asn Glu
    210                 215                 220

Arg Thr Leu Asp Phe His Asp Ser Asn Val Lys Asn Leu Tyr Asp Lys
225                 230                 235                 240

Val Arg Leu Gln Leu Arg Asp Asn Ala Lys Glu Leu Gly Asn Gly Cys
                245                 250                 255

Phe Glu Phe Tyr His Lys Cys Asp Asn Glu Cys Met Glu Ser Val Arg
            260                 265                 270

Asn Gly Thr Tyr Asp Tyr Pro Gln Tyr Ser Glu Glu Ala Arg Leu Lys
        275                 280                 285

Arg Glu Glu Ile Ser Gly Val Lys Leu Glu Ser Ile Gly Ile Tyr Gln
    290                 295                 300

Ile Leu Ser Ile Tyr Ser Thr Val Ala Ser Ser Leu Ala Leu Ala Ile
305                 310                 315                 320

Met Val Ala Gly Leu Ser Leu Trp Met Cys Ser Asn Gly Ser Leu Gln
                325                 330                 335

Cys Arg Ile Cys Ile
            340
```

<210> SEQ ID NO 16
<211> LENGTH: 2274
<212> TYPE: DNA
<213> ORGANISM: Influenza A virus
<220> FEATURE:
<221> NAME/KEY: misc_feature
<223> OTHER INFORMATION: PB1 sequence

<400> SEQUENCE: 16

```
atggatgtca atccgacttt acttttcttg aaagtaccag tgcaaaatgc tataagtacc      60
accttcccctt atactggaga ccctccatac agccatggaa cagggacagg atacaccatg    120
gacacagtca acagaacaca ccaatattca gaaaagggga agtggacaac aaacacagag    180
actggagcac cccaactcaa cccgattgat ggaccactac ctgaggataa tgagcccagt    240
gggtacgcac aaacagattg tgtattggaa gcaatggctt ccttgaaga atcccaccca    300
gggatctttg aaaactcgtg tcttgaaacg atggaaattg ttcaacaaac aagagtggat    360
aaactgaccc aaggtcgcca gacctatgac tggacattga atagaaacca accggctgca    420
actgctttgg ccaacactat agaaatcttc agatcgaacg gtctaacagc caatgaatcg    480
ggacggctaa tagatttcct caaggatgtg atggagtcaa tggataagga agaaatggag    540
ataacaacac atttccagag aaagagaagg gtgagggaca catgaccaa gaaaatggtc    600
acacaaagaa cataggggaa gaaaaaacaa aggctgaaca aaaagagcta cctgataaga    660
gcactgacac tgaacacaat gacaaaagat gcagaaagag gcaaattgaa gaggcgagcg    720
attgcaacac ccggaatgca atcagagga ttcgtgtact ttgttgaaac actagcgagg    780
agtatctgtg agaaacttga gcaatctgga ctcccagtcg gagggaatga aagaaggct    840
aaattggcaa acgtcgtgag gaagatgatg actaactcac aagatactga actctccttt    900
acaattactg gagacaatac caaatggaat gagaatcaga atcctaggat gtttctggca    960
atgataacgt acatcacaag gaaccagcca gaatggtttc ggaatgtctt aagcatagct   1020
cctataatgt tctcaaacaa aatggcgaga ctaggaaaag gatacatgtt cgaaagtaag   1080
agcatgaagt tacgaacaca ataccagca gaaatgcttg caaacattga tcttaaatac   1140
ttcaatgaat taacgaaaaa gaaaattgag aaaataaggc ctctattaat agatggtaca   1200
gcctcattga gccctggaat gatgatgggc atgttcaaca tgctgagtac agtcctagga   1260
gtttcaatcc tgaatcttgg acagaaaagg tacaccaaaa ccacatattg gtgggacgga   1320
ctccaatcct ctgatgattt cgctctcatc gtaaatgcac cgaatcatga gggaatacaa   1380
gcaggagtgg ataggtttta taggacttgt aaactagttg gaatcaatat gagcaagaag   1440
aagtcttaca taaatcggac agggacattt gaattcacga gcttttctta ccgctatgga   1500
tttgtagcca atttcagtat ggagctgccc agttttggag tgtctggaat taatgaatcg   1560
gccgacatga gcattggtgt tacagtgata aaaaacaata tgataaacaa cgaccttggg   1620
ccagcaacag ctcagatggc tcttcagtta ttcatcaagg actacagata cacataccga   1680
tgccacagag gggatacgca aatccaaaca aggagatcat tcgagctgaa gaagctgtgg   1740
gagcaaaccc gttcaaaggc aggactgttg gtttcagatg gaggaccaaa tctatacaat   1800
atccgaaacc tccatattcc tgaagtctgc ttaaaatggg aattgatgga tgaagattac   1860
cagggcagac tgtgtaatcc tctgaatcca ttcgtcagcc ataaggaaat tgaatctgtc   1920
aacaatgctg tagtaatgcc agctcatggc ccggccaaga gtatgaaata tgatgccgtt   1980
gcaactacac attcatggat tcctaaaagg aaccgttcca ttctcaatac gagtcaaagg   2040
ggaattcttg aggatgaaca gatgtaccag aagtgctgca atctattcga gaaattcttc   2100
cccagcagtt catatcggag gccagttgga atttccagca tggtggaggc catggtgtct   2160
agggcccgaa ttgacgcacg aatcgatttc gagtctggaa ggattaagaa agaagagttt   2220
gccgagatca tgaagatctg ttccaccatt gaagaactca gacggcaaaa atag         2274
```

<210> SEQ ID NO 17
<211> LENGTH: 757
<212> TYPE: PRT
<213> ORGANISM: Influenza A virus
<220> FEATURE:
<221> NAME/KEY: MISC_FEATURE
<223> OTHER INFORMATION: PB1 sequence

<400> SEQUENCE: 17

```
Met Asp Val Asn Pro Thr Leu Leu Phe Leu Lys Val Pro Val Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Ile Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Ile Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Lys Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365
```

Pro Ala Glu Met Leu Ala Asn Ile Asp Leu Lys Tyr Phe Asn Glu Leu
370                 375                 380

Thr Lys Lys Ile Glu Lys Ile Arg Pro Leu Leu Ile Asp Gly Thr
385                 390                 395                 400

Ala Ser Leu Ser Pro Gly Met Met Gly Met Phe Asn Met Leu Ser
            405                 410                 415

Thr Val Leu Gly Val Ser Ile Leu Asn Leu Gly Gln Lys Arg Tyr Thr
            420                 425                 430

Lys Thr Thr Tyr Trp Trp Asp Gly Leu Gln Ser Ser Asp Phe Ala
        435                 440                 445

Leu Ile Val Asn Ala Pro Asn His Glu Gly Ile Gln Ala Gly Val Asp
450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
            755

<210> SEQ ID NO 18
<211> LENGTH: 99
<212> TYPE: DNA

```
<213> ORGANISM: Artificial Sequence
<220> FEATURE:
<223> OTHER INFORMATION: Promoter
<220> FEATURE:
<221> NAME/KEY: misc_feature
<223> OTHER INFORMATION: mH5 promoter

<400> SEQUENCE: 18
aaaaattgaa aataaataca aaggttcttg agggttgtgt taaattgaaa gcgagaaata      60
atcataaata atttcattat cgcgatatcc gttaagttt                            99

<210> SEQ ID NO 19
<211> LENGTH: 39
<212> TYPE: DNA
<213> ORGANISM: Artificial Sequence
<220> FEATURE:
<223> OTHER INFORMATION: Synthetic promoter
<220> FEATURE:
<221> NAME/KEY: misc_feature
<223> OTHER INFORMATION: Synthetic early/late selP promoter

<400> SEQUENCE: 19
aaaaattgaa attttatttt ttttttttgg aatataaat                            39
```

RECOMBINANT VIRAL VECTORS AND METHODS FOR INDUCING A HETEROSUBTYPIC IMMUNE RESPONSE TO INFLUENZA A VIRUSES

FIELD OF THE INVENTION

The present invention relates to recombinant viral vectors and methods of using the recombinant viral vectors to induce an immune response to influenza A viruses. The invention provides recombinant viral vectors based, for example, on the non-replicating modified vaccinia virus Ankara. When administered according to methods of the invention, the recombinant viral vectors are designed to be cross-protective and induce heterosubtypic immunity to influenza A viruses.

BACKGROUND OF THE INVENTION

Human influenza or "the flu" is a respiratory disease that is caused by influenza A and B viruses. Epidemics of influenza cause significant illness and death worldwide each year, and vaccination is the most straightforward strategy to prevent infection and disease. Traditional influenza vaccines expose the recipient to influenza virus proteins causing the recipient to mount an immune response to the proteins. Proteins (or polypeptides) used in vaccines are commonly called "antigens." The commonly used seasonal influenza vaccines are based on the major antigen of the viruses, the hemagglutinin (HA). There are numerous influenza A subtypes having different HA antigens. Influenza A subtypes are divided and classified based on the HA and neuraminidase (NA) proteins that are expressed by the viruses. The influenza A subtype nomenclature is based on the HA subtype (of the sixteen different HA genes known in the art) and the NA subtype (of the nine different NA genes known in the art). Exemplary subtypes, include, but are not limited to, H5N1, H1N1 and H3N2. There are also variants of the influenza A subtypes which are referred to as "strains." For example, the virus A/VietNam/1203/2004 is an influenza A virus, subtype H5N1, with a strain name A/VietNam/1203/2004.

Protection from the seasonal vaccines based on the HA is strain-specific and new strains emerge constantly, so the classical influenza vaccines have to be re-formulated each year in an attempt to match the currently circulating strains. See, Lambert and Fauci 2010. It is therefore highly desirable for next generation vaccines to be cross-protective and induce heterosubtypic immunity, i.e., vaccines against one subtype that protect or partially protect against challenge infection with influenza A of different subtypes.

The current 'universal vaccines' (i.e., vaccines designed to elicit heterosubtypic immunity) that are under development are mainly based on the more conserved internal influenza virus genes including the influenza matrix proteins (M1 and M2) (Schotsaert et al. 2009), the nucleoprotein (NP) and conserved parts of the HA (Bommakanti et al. 2010; Steel et al. 2010). The polymerase proteins PA, PB1 and PB2 also induce substantial T cell responses and may be also relevant targets (Assarsson et al. 2008; Greenbaum et al. 2009; Lee et al. 2008).

Next generation influenza vaccines currently under development include recombinant proteins, synthetic peptides, virus-like particles (VLPs), DNA-based vaccines and viral vector vaccines (Lambert and Fauci, supra). The advantage of using live viral vectors is their known property to induce high levels of cellular immunity, in particular CD8 T cells. Among the most promising viral vectors are vaccinia virus-based live vaccines (Rimmelzwaan and Sutter 2009) and adenovirus-based vectors (Hoelscher et al. 2006; Hoelscher et al. 2007; Price et al. 2010; Zhou et al. 2010). Single-dose mucosal immunization using an adenovirus construct expressing NP and M2, for instance, provided protection from virulent H5N1, H3N2 and H1N1 viruses (Price et al, supra). In a further study (Price et al. 2009), DNA vaccination with nucleoprotein (NP) and matrix 2 (M2) plasmids followed by boosting with antigen-matched recombinant adenovirus (rAd) provided robust protection against virulent H1N1 and H5N1 challenges in mice and ferrets.

Recombinant vaccines based on modified vaccinia virus Ankara (MVA) have been used in many non-clinical and clinical studies. MVA has proven to be exceptionally safe. No significant side effects have been obtained when MVA was administered to more than 120,000 human patients in the context of the smallpox eradication. Due to a block in virion morphogenesis the highly attenuated vaccinia virus strain fails to productively replicate in human and most other mammalian cells. Nevertheless, the ability to express viral and foreign genes in the early and late stage is retained. These characteristics make MVA a promising live vaccine vector that induces humoral and cellular immune responses and that exhibits a high safety profile.

U.S. Pat. Nos. 6,998,252; 7,015,024; 7,045,136 and 7,045,313 relate to recombinant poxviruses, such as vaccinia.

MVA-based vaccines have been used in clinical studies, for instance, against HIV, tuberculosis, malaria and cancer. In all of these studies, at least two doses were used. The human dose of an MVA-based vaccine was $5\times10^7$ to $5\times10^8$ PFU as applied in clinical trials (Brookes et al. 2008; Cebere et al. 2006; Tykodi and Thompson 2008;).

MVA has been used recently as a vector in pandemic H5N1 (Kreijtz et al. 2008; Kreijtz et al. PLoS One 2009; Kreijtz et al. Vaccine 2009; Kreijtz et al. J. Infect. Dis. 2009; Kreijtz et al. 2007; Mayrhofer et al., 2009; Poon et al. 2009) and H1N1 (Hessel et al. 2010; Kreijtz et al., J. Infect. Dis. 2009) influenza research. An MVA-based vaccine expressing NP and M1 is currently being tested in an ongoing clinical trial (Berthoud et al. 2011).

Thus, there remains a need in the art for a more broadly protective influenza vaccine.

DETAILED DESCRIPTION

The present invention provides recombinant viruses (also referred to as recombinant viral vectors herein) useful for generating a heterosubtypic immune response to influenza A viruses. The recombinant viruses are recombinant vaccinia viruses, such as recombinant MVA or other non-replicating or replicating vaccinia virus known in the art. Non-replicating vaccinia viruses include, but are not limited to, defective vaccinia Lister (dVV), MVA-575 (ECACC V00120707), MVA-BN (ECACC V00083008), MVA-F6 and MVA-M4 (Antoine et al. 1998). In some embodiments, the recombinant viruses encode a fusion protein (hlHA/M2e) comprising an influenza A hemagglutinin deletion mutant "headless HA" (hlHA) with at least one influenza A M2 external domain (M2e) insert; an hlHA/M2e fusion protein and an influenza A nucleoprotein (NP); or an hlHA and NP. The recombinant viruses of the invention may further encode an influenza A matrix protein 1 (M1) and/or an influenza A polymerase PB1. When administered according to methods of the invention, the recombinant viruses are cross-protective and induce heterosubtypic humoral and cellular immune responses (including CD8 and CD4 T cell responses). The recombinant viruses are therefore contemplated to be useful as universal influenza A vaccines in humans.

In some embodiments, the hlHA amino acid sequence encoded by an open reading frame in recombinant viruses of the invention may be, for example, the hlHA amino acid sequence set out in SEQ ID NO: 15 (based on A/VietNam/1203/2004 H5N1 HA NCBI Genbank AAW80717 which is SEQ ID NO: 3). The hlHA of SEQ ID NO: 15 comprises a signal sequence, the HA1 residues 17-58 of SEQ ID NO: 3, a linker peptide of four glycines, the HA1 residues 290-343 of SEQ ID NO: 3 and the HA2 stalk region residues 344-568 of SEQ ID NO: 3.

In some embodiments, the hlHA/M2e fusion protein amino acid sequence encoded by an open reading frame in recombinant viruses of the invention may be, for example, the hlHA/M2e fusion protein amino acid sequence set out in SEQ ID NO: 2. The fusion protein of SEQ ID NO: 2 comprises a signal sequence, the HA1 residues 17-58 of SEQ ID NO: 3, a linker peptide of three glycines (SEQ ID NO: 4), the M2e of H5N1 (SEQ ID NO: 5 based on A/VietNam/1203/2004 H5N1 NCBI Genbank ABP35634), a six-amino acid linker GSAGSA (SEQ ID NO: 9), the M2e of H1N1 (equivalent to H2N2 and H3N2) (SEQ ID NO: 6 based on A/New York/3315/2009 H1N1 NCBI Genbank ACZ05592), a six-amino acid linker GSAGSA (SEQ ID NO: 9), the M2e of H9N2 (SEQ ID NO: 7 based on A/chicken/Korea/SH0913/2009 H9N2 NCBI Genbank ADQ43641), a six-amino acid linker GSAGSA (SEQ ID NO: 9), the M2e of H7N2 (SEQ ID NO: 8 based on A/New York/107/2003 H7N2 NCBI Genbank ACC55276), a linker peptide of three glycines (SEQ ID NO: 4), the HA1 residues 290-343 of SEQ ID NO: 3 and the HA2 region residues 344-568 of SEQ ID NO: 3.

In some embodiments, the hlHA/M2e fusion protein may comprise one, two, three or four of the M2e polypeptides of SEQ ID NOs: 5, 6, 7 and 8. The hlHA/M2e fusion protein may comprise an influenza A M2e polypeptide other than an M2e polypeptide of SEQ ID NOs: 5, 6, 7, and 8.

In some embodiments, the NP amino acid sequence encoded by an open reading frame in recombinant viruses of the invention may be, for example, the NP amino acid sequence set out in SEQ ID NO: 13 (based on A/VietNam/1203/2004 H5N1 NP NCBI Genbank AAW80720). In some embodiments, the M1 amino acid sequence encoded by an open reading frame in recombinant viruses of the invention may be, for example, the M1 amino acid sequence set out in SEQ ID NO: 11 (based on A/VietNam/1203/2004 H5N1 M1 Genbank AAW80726). In some embodiments, the PB1 amino acid sequence encoded by an open reading frame in recombinant viruses of the invention may be, for example, the PB1 amino acid sequence set out in SEQ ID NO: 17 (based on A/VietNam/1203/2004 H5N1 PB1 Genbank AAW80711).

The invention contemplates that polypeptides encoded by an open reading frame in a recombinant virus may vary in sequence from SEQ ID NO: 2, 5, 6, 7, 8, 11, 13, 15 and/or 17 if the polypeptides retain the ability to induce a protective immune response when the recombinant virus is administered to an individual. In these embodiments, the polypeptide may be about 80%, about 85%, about 90%, about 91%, about 92%, about 93%, about 94%, about 95%, about 95%, about 97%, about 98% or about 99% identical to SEQ ID NO: 2, 5, 6, 7, 8, 11, 13, 15 and/or 17.

In other embodiments, hlHA/M2e fusion proteins, hlHA polypeptides and NP polypeptides encoded by recombinant viruses of the invention may be based on the same or different influenza A subtypes including, but not limited to, any combination of H1 to H16 and N1 to N9 (including H1N1, H2N1, H3N1, H4N1, H5N1, H6N1, H7N1, H8N1, H9N1, H10N1, H11N1, H12N1, H13N1, H14N1, H15N1, H16N1; H1N2, H2N2, H3N2, H4N2, H5N2, H6N2, H7N2, H8N2, H9N2, H10N2, H11N2, H12N2, H13N2, H14N2, H15N2, H16N2; H1N3, H2N3, H3N3, H4N3, H5N3, H6N3, H7N3, H8N3, H9N3, H10N3, H11N3, H12N3, H13N3, H14N3, H15N3, H16N3; H1N4, H2N4, H3N4, H4N4, H5N4, H6N4, H7N4, H8N4, H9N4, H10N4, H11N4, H12N4, H13N4, H14N4, H15N4, H16N4; H1N5, H2N5, H3N5, H4N5, H5N5, H6N5, H7N5, H8N5, H9N5, H10N5, H11N5, H12N5, H13N5, H14N5, H15N5, H16N5; H1N6, H2N6, H3N6, H4N6, H5N6, H6N6, H7N6, H8N6, H9N6, H10N6, H11N6, H12N6, H13N6, H14N6, H15N6, H16N6; H1N7, H2N7, H3N7, H4N7, H5N7, H6N7, H7N7, H8N7, H9N7, H10N7, H11N7, H12N7, H13N7, H14N7, H15N7, H16N7; H1N8, H2N8, H3N8, H4N8, H5N8, H6N8, H7N8, H8N8, H9N8, H10N8, H11N8, H12N8, H13N8, H14N8, H15N8, H16N8; H1N9, H2N9, H3N9, H4N9, H5N9, H6N9, H7N9, H8N9, H9N9, H10N9, H11N9, H12N9, H13N9, H14N9, H15N9, and H16N9). In some embodiments the influenza A subtype is a pandemic influenza A. Exemplary pandemic influenza subtypes include, but are not limited to, H1N1, H2N2, H3N2 and H5N1.

A list of identified Influenza A strains, including influenza A H1N1 strains, is available from the World Health Organization (WHO) and United States Centers for Disease Control (CDC) databases of Influenza A subtypes. The National Center for Biotechnology Information (NCBI) database maintained by the United States National Library of Medicine also maintains an updated database describing the length and sequence of HA, M2, NP, M1 and PB1 genes of viruses of influenza A species. Strains listed by these organizations and strains described in other commercial and academic databases, or in literature publications and known in the art, are contemplated for use in the invention. It is also contemplated that additional influenza A strains hereafter identified and isolated are also useful in the invention as sources of influenza A protein sequences. Accordingly, any strain specifically exemplified in the specification and those known or after discovered in the art are amenable to the recombinant vaccinia virus, pharmaceutical compositions, and methods of the invention. Exemplary strains include, but are not limited to, the strains in Table 1 below. The table also lists exemplary genes and associated database accession numbers of those strains.

TABLE 1

| Virus subtype | Inserted Influenza gene | Virus strain | NCBI gene acc no. | NCBI amino acid acc no. |
| --- | --- | --- | --- | --- |
| H5N1 | HA | A/Viet Nam/1203/2004 | AY818135 | AAW80717 |
| H5N1 | NP | A/Viet Nam/1203/2004 | AY818138 | AAW80720 |
| H5N1 | M1 | A/Viet Nam/1203/2004 | AY818144 | AAW80726 |
| H5N1 | PB1 | A/Viet Nam/1203/2004 | AY818129 | AAW80711 |

TABLE 1-continued

| Virus subtype | Inserted Influenza gene | Virus strain | NCBI gene acc no. | NCBI amino acid acc no. |
|---|---|---|---|---|
| H5N1 | M2 | A/Viet Nam/1203/2004 | EF541453 | ABP35634 |
| H1N1 sw | M2 | A/California/07/09 | FJ969537 | ACP44185 |
| H1N1 | M2 | A/New York/3315/2009 | CY050765 | ACZ05592 |
| H2N2 | M2 | A/Korea/426/68 | NC_007377 | YP_308853 |
| H3N2 | M2 | A/NewYork/392/2004 | NC_007367 | YP_308840 |
| H9N2 | M2 | A/chicken/Korea/SH0913/2009 | HQ221654 | ADQ43641 |
| H7N2 | M2 | A/New York/107/2003 | EU587373 | ACC55276 |
| H7N3 | M2 | A/chicken/Pakistan/34668/1995 | CY035834 | ACJ03948 |

In recombinant viruses of the invention, open reading frames encoding hlHA/M2e, hlHA, NP, M1 and/or PB1 may be codon-optimized for expression in human cells. In these embodiments, one or more (or all) of the naturally occurring codons in an open reading frame have been replaced in the codon-optimized open reading frame with codons frequently used in genes in human cells (sometimes referred to as preferred codons). Codons may be optimized to avoid repeat sequences to stabilize an open reading frame in the rMVA and/or to avoid unwanted transcription stop signals. Codon-optimization, in general, has been used in the field of recombinant gene expression to enhance expression of polypeptides in cells.

Gene cassettes encoding hlHA/M2e, hlHA, NP, M1 and PB1 in recombinant viruses of the invention include an open reading frame under the control of (i.e., operatively linked to) a promoter that functions (i.e., directs transcription of the open reading frame) in the recombinant vaccinia viruses. In exemplary embodiments, expression from gene cassettes is under the control of the strong early/late vaccinia virus mH5 promoter (SEQ ID NO: 18) or the synthetic early/late selP promoter (SEQ ID NO: 19) (Chakrabarti et al. 1997). In the gene cassettes of the invention the open reading frame is also operatively linked to a transcription stop signal such as a vaccinia virus early transcription stop signal.

In one aspect, the invention provides recombinant vaccinia virus comprising a gene cassette encoding an influenza A hlHA/M2e fusion protein. In some embodiments, the recombinant vaccinia virus is a recombinant MVA comprising a gene cassette expressing the hlHA/M2e fusion protein set out in SEQ ID NO: 2. In some embodiments, the recombinant vaccinia virus further comprises a gene cassette expressing the M1 protein (for example, the M1 set out in SEQ ID NO: 11) and/or a gene cassette expressing the PB1 protein (for example, the PB1 protein set out in SEQ ID NO: 17).

In another aspect, the invention provides recombinant vaccinia virus comprising a first gene cassette encoding an influenza A hlHA/M2e fusion protein. and a second gene cassette encoding an influenza NP. In some embodiments, the recombinant vaccinia virus is a recombinant MVA comprising a first gene cassette expressing the hlHA/M2e fusion protein set out in SEQ ID NO: 2 and a second gene cassette expressing the NP set out in SEQ ID NO: 13. In some embodiments, the recombinant vaccinia virus further comprises a gene cassette expressing the M1 protein (for example, the M1 set out in SEQ ID NO: 11) and/or a gene cassette expressing the PB1 protein (for example, the PB1 protein set out in SEQ ID NO: 17).

In yet another aspect, the invention provides recombinant vaccinia virus comprising a first gene cassette encoding an influenza A hlHA and a second gene cassette encoding an influenza NP. In some embodiments, the recombinant vaccinia virus is a recombinant MVA comprising a first gene cassette expressing the hlHA set out in SEQ ID NO: 15 and a second gene cassette expressing the NP set out in SEQ ID NO: 13. In some embodiments, the recombinant vaccinia virus further comprises a gene cassette expressing the M1 protein (for example, the M1 set out in SEQ ID NO: 11) and/or a gene cassette expressing the PB1 protein (for example, the PB1 protein set out in SEQ ID NO: 17).

In recombinant vaccinia viruses of the invention, the gene cassettes may be inserted in non-essential regions of the vaccinia virus genome, such as the deletion I region, the deletion II region, the deletion III region, the deletion IV region, the thymidine kinase locus, the D4R/5R intergenic region, or the HA locus. In exemplified embodiments of recombinant MVA, the insertion of the hlHA/M2e and hlHA gene cassettes is in the D4R/5R intergenic region and the insertion of the NP gene cassette is in the deletion III region. The recombinant MVA is derived from an MVA free of bovine spongiform encephalopathy (BSE) such as MVA74 LVD6 obtained from the National Institutes of Health.

The recombinant viruses of the invention may be formulated as pharmaceutical compositions according to methods known in the art. In some embodiments, the recombinant viruses are formulated as described in International Publication No. WO 2010/056991.

The invention provides methods of inducing a heterosubtypic influenza A immune response in an individual comprising administering compositions of recombinant vaccinia virus of the invention to the individual. In the methods, the composition may be administered as a single dose, a double dose or multiple doses. The administration route in humans may be inhalation, intranasally, orally, and parenterally. Examples of parenteral routes of administration include intradermal, intramuscular, intravenous, intraperitoneal and subcutaneous administration. The range of the human immunization dose may be about $10^6$ to about $10^9$ PFU. The methods of the invention induce humoral and cellular immune responses in the individual. Moreover, in embodiments of the invention the methods induce a protective immune response in the individual. The protective immune response may be where the individual exhibits no symptoms of infection, a reduction in symptoms, a reduction in virus titer in tissues or nasal secretions, and/or complete protection against infection by influenza virus.

The invention also provides kits for administering recombinant vaccinia virus of the invention packaged in a manner which facilitates their use to practice methods of the invention. In one embodiment, such a kit includes a recombinant virus or composition described herein, packaged in a container such as a sealed bottle or vessel, with a label affixed to the container or included in the package that describes use of the compound or composition in practicing the method. Preferably, the recombinant virus or composition is packaged in a unit dosage form. The kit may further include a device suitable for administration according to a specific route of administration or for practicing a screening assay. Preferably, the kit contains a label that describes use of the recombinant vaccinia virus. In some embodiments, the kit comprises instructions for administration to a human subject.

Also provided are methods of producing a recombinant vaccinia virus expressing a gene cassette of the invention. As illustrated with MVA, the methods comprise the steps of: a) infecting primary chicken embryo cells or a suitable permanent cell line (e.g., avian) with MVA, b) transfecting the infected cells with a plasmid comprising the gene cassette and comprising DNA flanking the gene cassette that is homologous to a non-essential region of the MVA genome, c) growing the cells to allow the plasmid to recombine with the MVA genome during replication of the MVA in chicken cells thereby inserting the gene cassette into the MVA genome in the non-essential region, and d) obtaining the recombinant MVA produced. Exemplary chicken embryo cells are described in U.S. Pat. No. 5,391,491. (Slavik et al. 1983) Other avian cells (e.g., DF-1) are also contemplated. In the methods, the non-essential MVA region is the deletion I region, the deletion II region (Meyer et al. 1991), the deletion III region (Antoine et al. 1996), the deletion IV region (Meyer et al., supra; Antoine et al. 1998) the thymidine kinase locus (Mackett et al. 1982), the D4R/5R intergenic region (Holzer et al. 1998), or the HA locus (Antoine et al. supra). In one exemplified embodiment, the insertion is in the deletion III region. In another exemplified embodiment, the insertion is in the D4R/5R intergenic region. If two gene cassettes are to be inserted, the two are inserted in different non-essential regions. Gene cassettes may additionally be inserted into any other suitable genomic region or intergenomic regions.

Other vertebrate cell lines are useful for culture and growth of vaccinia virus of the invention. Exemplary vertebrate cells useful to culture vaccinia virus of the invention include, but are not limited to, MRC-5, MRC-9, CV-1 (African Green monkey), HEK (human embryonic kidney), PerC6 (human retinoblast), BHK-21 cells (baby hamster kidney), BSC (monkey kidney cell), LLC-MK2 (monkey kidney) and permanent avian cell lines such as DF-1.

Vero cells are an accepted cell line for production of viral vaccines according to the World Health Organization. In some embodiments, recombinant replicating vaccinia virus of the invention are produced in Vero cells.

Additional aspects and details of the invention will be apparent from the following examples, which are intended to be illustrative rather than limiting.

FIGURES

FIG. 1 shows the amino acid sequence (SEQ ID NO: 15) of the headless HA protein encoded by recombinant MVA (rMVA) of the invention. The protein contains a signal sequence (grey), HA1 residues (red), a linker peptide of four glycines (black), HA1 residues (red), and the HA2 stalk region (black). Cysteines 58 and 63 and the polybasic cleavage site (amino acids 112-119) are underlined.

FIG. 2 shows the nucleotide sequence (SEQ ID NO: 14) of the headless HA protein encoded by rMVA of the invention.

FIG. 3 shows the amino acid sequence (SEQ ID NO: 2) of headless HA/M2e fusion protein. The designed protein contains a signal sequence (grey), HA1 residues (red), a linker peptide of three glycines (black), the M2e of H5N1 (blue), the six amino acid linker GSAGSA (black), the M2e of H1N1 (equivalent to H2N2, H3N2; green), the six amino acid linker GSAGSA, the M2e of H9N2 (orange), the six amino acid linker GSAGSA, the M2e of H7N2 (pink), a linker peptide of three glycines (black), HA1 residues (red) and the HA2 stalk region (black). The polybasic cleavage site (amino acids 224-231) is underlined.

FIG. 4 shows the nucleotide sequence (SEQ ID NO: 1) of the headless HA/M2e fusion protein encoded by rMVA of the invention.

FIG. 5 shows single-insert rMVAs containing influenza genes. FIG. 5A indicates the hlHA, hlHA/M2e, M2, PB1, or M1 gene cassettes that are located in the recombinant MVA D4R/D5R intergenic locus, at the position corresponding to nucleotide 87,281 of wild type MVA (Antoine et al, supra). FIG. 5B indicates the NP gene cassette is located in the del lll locus at the position corresponding to nucleotide 142,992 of wild type MVA.

FIG. 6 shows a Western Blot of chicken cell lysates tested for influenza virus antigens. A) Expression of headless HA and the headless HA/M2e fusion protein using a detection antibody directed against HA. Lane 1, protein ladder, size in kDa; lane 2, MVA-hlHA; lane 3, MVA-hlHA/M2e; lane 4, MVA wt (negative control); and lane 5, MVA-HA-VN (positive control). B) Expression of the headless HA/M2e fusion protein using a detection antibody directed against M2. Lane 1, protein ladder, size in kDa; lane 2, MVA-M2-VN; lane 3, MVA-hlHA/M2e; and lane 4, MVA wt (negative control). The recombinant MVA-M2-VN expresses the M2 protein (weak band below 15 kDa). The anti-M2-antibody binds a peptide at the N-terminus of the M2 protein; thus the expression of the hlHA/M2e fusion protein is also detectable at around 70 kDa (lane 3).

Figure 7:
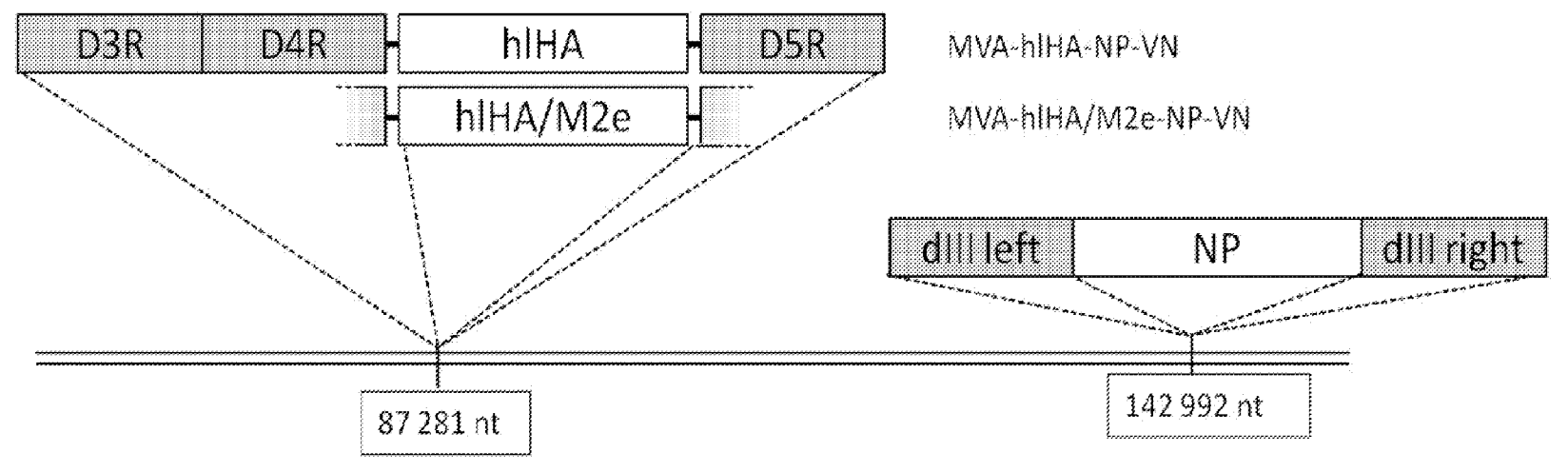

FIG. 7 shows double-insert rMVAs containing influenza genes. The hlHA or hlHA/M2e gene cassette is located in the D4R/D5R intergenic locus, at the position corresponding to nucleotide 87,281 of wild type MVA. The NP gene cassette is located in the del lll locus at the position corresponding to nucleotide 142,992 of the wild type MVA.

FIG. 8 shows a Western Blot of chicken cell lysates tested for influenza virus antigens. A) Expression of headless HA and the headless HA/M2e fusion protein using a detection antibody directed against HA. Lanes 1 and 7, protein ladder, size in kDa; lane 2, MVA-HA-VN (positive control); lane 3, MVA-hlHA; lane 4, MVA wt (negative control); lane 5, MVA-hlHA/M2e-NP; and lane 6, MVA-hlHA-NP. The hlHA/M2e fusion protein expressed by MVA-hlHA/M2e is visible at around 70 kDa (lane 5). The lower bands at around 40 kDa represent the hlHA expressed by MVA-hlHA-NP and MVA-hlHA. The control construct (MVA-HA-VN), expressing the full length HA protein express the HA0 (band around 80 kDa), the HA1 (band around 55 kDa, and the HA2 (band around 25 kDa). The expression of the HA2 protein is also visible in lanes 3, 5 and 6 as the hlHA and hlHA/M2e proteins also contain the polybasic cleavage site. The specific HA bands are absent in the negative control (lane 4). B) NP expression detected with an NP-specific antibody. Lane 1, protein ladder, size in kDa; lane 2, MVA-D3-NP-VN; lane 3, MVA-hlHA-NP; lane 4, MVA-hlHA/M2e-NP; and lane 5, MVA wt (negative control).

Figure 9:
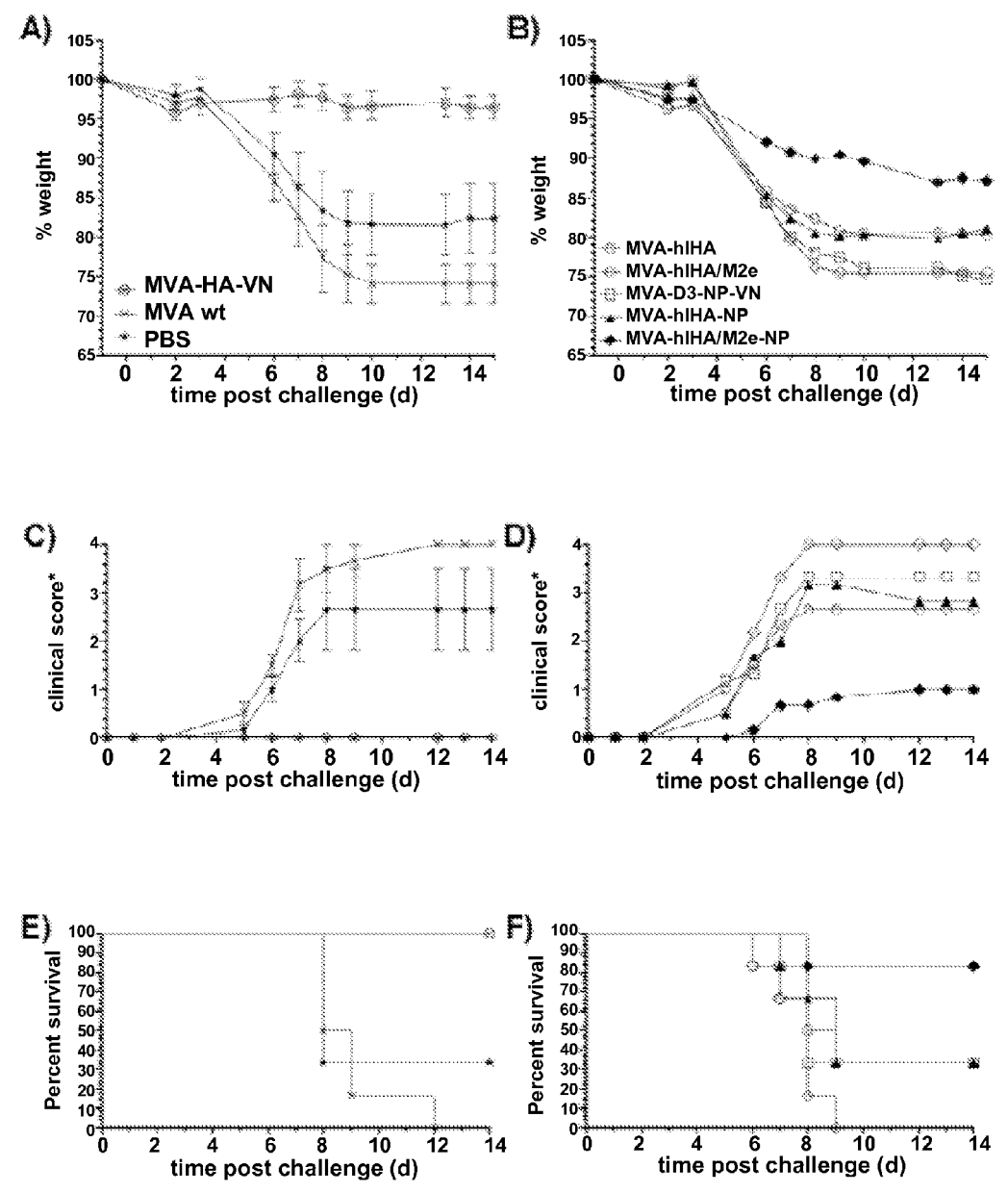

FIG. 9 shows monitoring of weight (A, B), clinical symptoms (C, D) and survival (E, F) after vaccination with recombinant MVAs and challenge with H5N1. As controls, mice were vaccinated with MVA-HA-VN, expressing the full-length HA of A/Vietnam/1203/2004, wt MVA or were treated with PBS (panels A, C, E). Mice were vaccinated with the single recombinant MVA-hlHA, MVA-hlHA/M2e, MVA-NP-VN or the double recombinants MVA-hlHA-NP and MVA-hlHA/M2e-NP (panels B, D, F). After challenge with wild-type H5N1, mice were monitored for 14 days.

FIG. 10 shows monitoring of weight (A, B), clinical symptoms (C, D) and survival (E, F) after vaccination with recombinant MVAs and challenge with H9N2 virus. As controls, mice were vaccinated with the whole virus preparation of H9N2, wt MVA or were treated with PBS (panels A, C, E). Mice were vaccinated with the single recombinant MVA-hlHA, MVA-hlHA/M2e, MVA-NP-VN or double recombinant MVA-hlHA-NP and MVA-hlHA/M2e-NP (panels B, D, F). After challenge with virulent mouse-adapted H9N2 influenza virus, mice were monitored for 14 days.

Figure 11:
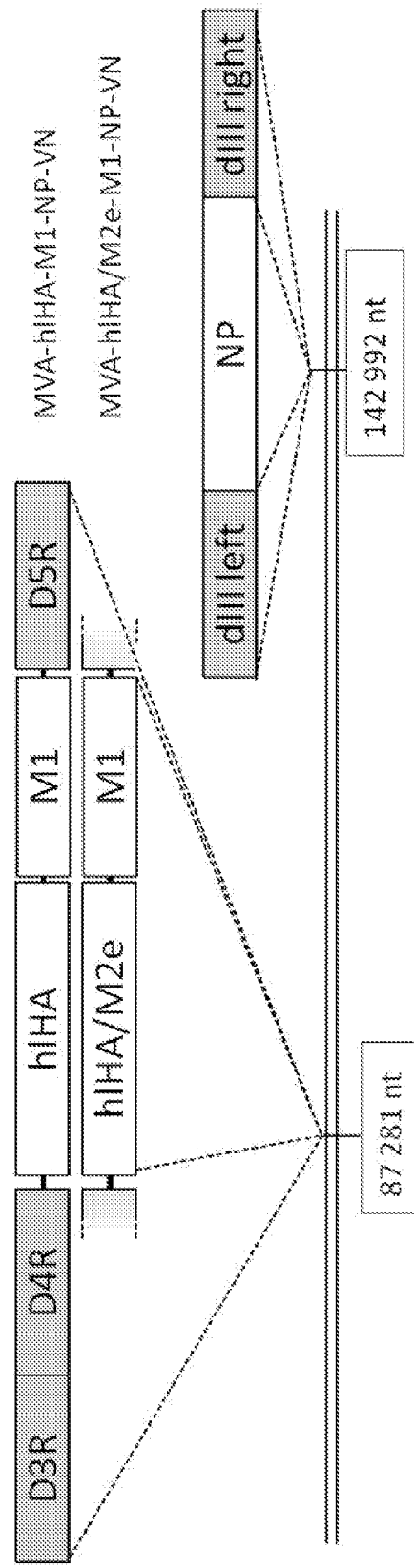

FIG. 11 shows triple-insert rMVAs containing influenza genes. The hlHA or hlHA/M2e and M1gene cassettes will be located in the D4R/D5R intergenic locus, at the position 87,281 nt of the wt MVA sequence. The NP gene cassette will be located in the del III locus at the position 142,992 nt of the wt MVA sequence.

EXAMPLES

The present invention is illustrated by the following examples wherein Example 1 describes the choice and design of influenza A antigens in exemplary recombinant MVA of the invention, Example 2 details the production of single-insert recombinant MVAs, Example 3 describes animal experiments with the single-insert MVAs, Example 4 details the production of double-insert recombinant MVAs, Example 5 describes animal experiments with the double-insert MVAs, Example 6 details the production of triple-insert recombinant MVAs and Example 7 describes animal experiments with the triple-insert MVAs.

Example 1

Choice and Design of Influenza A Antigens

Influenza headless HA, a headless HA/M2e fusion protein, NP, M1, M2 and PB1 were the influenza A antigens chosen to be encoded by exemplary recombinant MVA of the invention.

Monoclonal antibodies against the HA stalk domain, the HA2 region, are broadly cross-reactive and neutralize several subtypes of viruses (Ekiert et al. 2009; Kashyap et al. 2008; Okuno et al. 1993; Sanchez-Fauquier et al. 1987; Sui et al. 2009; Throsby et al. 2008). The antibodies target the HA2 region of the molecule and presumably act by preventing the conformational change of HA at low pH, thus presumably blocking fusion of viral and host membranes during influenza infection. However, the production of soluble, native (neutral pH-like) HA2 immunogen has proven to be difficult, owing to the metastable nature of HA (Chen et al. 1995). To induce an immune response against the neutral pH conformation, a headless HA was chosen as an antigen. The headless HA consists of two HA1 regions that interact with an HA2 subunit, stabilizing the neutral pH conformation (Bommakanti et al., supra; Steel et al., supra).

The extracellular domain of the M2 protein (M2e, 23AS) is highly conserved across influenza A virus subtypes. In animals, M2e specific antibodies reduce the severity of infection with a wide range of influenza A virus strains (Fan et al. 2004; Neirynck et al. 1999). Many groups have reported M2e-based vaccine candidates in different forms (De Filette et al. 2008; Denis et al. 2008; Eliasson et al. 2008; Fan et al., supra; Neirynck et al., supra). Recently, Zhao et al. reported that a tetra-branched multiple antigenic peptide vaccine based on H5N1 M2e induced strong immune responses and cross protection against different H5N1 clades and even heterosubtypic protection from 2009 H1N1 (Zhao et al. 2010b; Zhao et al. 2010a).

Vaccination using vectors expressing the conserved influenza NP, or a combination of NP and matrix protein has been studied in animal models and various degrees of protection against both homologous and heterologous viruses have been demonstrated (Price et al., supra; Ulmer et al. 1993). NP elicit a robust $CD8^+$ T cell response in mice and in humans (McMichael et al., 1986; Yewdell et al., 1985) that, as epidemiological studies suggest, may contribute to resistance against severe disease following influenza A virus infection (Epstein 2006).

The headless HA included in rMVA of the invention is a new headless HA (hlHA) based on the VN/1203 influenza strain. The hlHA contains a polybasic cleavage site which is cleaved during expression from the rMVA exposing the fusion peptide for the immune system. The amino acid sequence of the hlHA is set out in FIG. 1 and in SEQ ID NO: 15. The nucleotide sequence of the MVA insert is set out FIG. 2 and SEQ ID NO: 14.

The amino acid sequence of the headless HA/M2e fusion protein included in rMVA of the invention is set out in FIG. 3 below and in SEQ ID NO: 2. The nucleotide sequence of the fusion protein is set out in FIG. 4 below and in SEQ ID NO: 1. In the fusion protein, the M2e domains of H5N1, H9N2, H7N2 and H1N1 (equivalent to H2N2, H3N2) form an M2e "head" on the hlHA. The four particular M2e domains were chosen to represent the M2e from seasonal and pandemic strains.

Example 2

Construction and Characterization of Single-Insert MVA Vectors

The following single-insert, recombinant MVA (rMVA) are utilized in the experiments described herein.

TABLE 2

| rMVA | Inserted influenza gene | NCBI gene acc no. |
|---|---|---|
| 1. MVA-hlHA | headless HA | based on AY818135 |
| 2. MVA-hlHA/M2e | headless HA/M2e fusion | based on AY818135 |
| 3. MVA-M1-VN | Matrix protein 1 | AY818144 |
| 4. MVA-M2-VN | Matrix protein 2 | EF541453 |
| 5. MVA-PB1-VN | Polymerase subunit PB1 | AY818129 |
| 6. MVA-mNP | Nucleoprotein | AY818138 |
| 7. Control MVA-HA-VN | Hemagglutinin | AY818135 |
| 8. Control MVA-wt | No insert | — |
| 9. Control PBS | No insert | — |

For construction of single-insert rMVA vectors expressing hlHA, the hlHA/M2e fusion protein or PB1, the hlHA, hlHA/M2e and PB 1 genes were chemically synthesized (Geneart, Inc., Regensburg, Germany). The synthetic genes are driven by the strong vaccinia early/late promoter mH5 (Wyatt et al. 1996) and terminated with a vaccinia virus specific stop signal downstream of the coding region that is absent internally. The gene cassettes were cloned in the plasmid pDM-D4R (Ricci et al., 2011) resulting in plasmids pDM-hlHA, pDM-hlHA/M2e and pDM-PB1-VN, respectively. The introduction of the foreign genes into the D4R/D5R intergenic region of MVA was done as described elsewhere (Ricci et al. 2011) resulting in viruses MVA-hlHA, MVA-hlHA/M2e, MVA-PB1-VN.

For the construction of the rMVA expressing M1, the M1 sequence (accession number AY818144) was placed downstream of the strong vaccinia early/late promoter selP (Chakrabarti et al. 1997) and cloned in pDM-D4R, resulting in pDM-M1-VN. The expression cassette of pDD4-M2-VN—including the M2 sequence (accession number EF541453) under the control of the mH5 promoter—was cloned in pDM-D4R resulting in pDM-M2-VN. The plasmids were then used for recombination with MVA according to Holzer et al, supra resulting in the viruses MVA-M1-VN and MVA-M2-VN, respectively as shown in FIG. 5A.

For the construction of single-insert MVAs expressing the NP protein, the NP expression cassette of pDD4-mH5-mNP-VN (Mayrhofer et al., supra) was cloned in plasmid pd3-lacZ-gpt, resulting in pd3-lacZ-mH5-NP-VN. Plasmid pd3-lacZ-gpt contains a lacZ/gpt selection marker cassette and a multiple cloning site (MCS) for insertion of genes of interest. The sequences are framed by genomic MVA sequences of the del III region. The marker cassette is destabilized by a tandem repeat of MVA del III flank, thus the final recombinant is free of any auxiliary sequences. The insertion plasmid directs the gene cassettes into the MVA deletion III (del III) region. After infection of primary chicken embryo cells with MOI 1, cells were transfected with pd3-lacZ-mH5-NP-VN according to the calcium phosphate technique (Graham and van der Eb 1973), resulting MVA-NP-VN shown in FIG. 5B. The MVA strain (MVA 1974/NIH clone 1) was kindly provided by B. Moss (National Institutes of Health). Recombinant virus is selected using the transient marker stabilization method (Scheiflinger et al, 1998).

The single-insert MVA vectors expressing the NP, PB1, M1, M2, hlHA, and hlHA/M2e were characterized by PCR and Western blot as described in Hessel et al, supra. Recombinant viruses were grown in CEC or DF-1 cells and purified by centrifugation through a sucrose cushion. Primary CEC were produced in-house and cultivated in Med199 (Gibco®) supplemented with 5% fetal calf serum (FCS). The DF-1 (CRL-12203) cell line was obtained from the ATCC (American Type Culture Collection) and cultivated in DMEM (Biochrom, Inc.) supplemented with 5% FCS.

The correct expression of the influenza proteins by the rMVAs was confirmed by Western blotting. For this purpose CEC or the permanent chicken cell line DF-1 were infected with a MOI of 0.1 and cell lysates were prepared 48-72 hrs post infections. The recombinant MVAs that express the hlHA (MVA-hlHA and MVA-hlHA/M2e) were analyzed in a Western blot using an anti-influenza A/Vietnam/1194/04 (H5N1) polyclonal serum (NIBSC 04/214) for detection. Donkey-anti-sheep alkaline phosphatase-conjugated IgG (Sigma Inc.) was used as a secondary antibody. The recombinant MVAs that express the M2 and M2e (MVA-M2-VN and MVA-hlHA/M2e) were analyzed in Western Blots using an anti-avian influenza M2 antibody binding a peptide present at the amino terminus of the H5N1 M2 (ProSci, Cat#4333). Goat-anti-rabbit alkaline phosphatase-conjugated IgG (Sigma Inc.) antibody was used as a secondary antibody. As shown in FIG. 6A, the recombinant MVAs expressing the hlHA (MVA-hlHA and MVA-hlHA/M2e) gene inserts induced expression of the HA containing antigens in avian DF-1 cells. The bands around 40 kDa in lane 2 represent the hlHA. The larger band at around 70 kDa in lane 3 represents the hlHA/M2e. The large band at around 80 kDa in lane 5 represents the HA0 hemagglutinin-precursor, which is cleaved into the HA1 and HA2 subunits represent by the bands at approximately 55 and 25 kDa. The specific hlHA, hlHA/M2e or HA bands are absent in the wild-type MVA control (lane 4).

FIG. 6B shows the M2 expression by MVA-M2-VN (lane 2) or MVA-hlHA/M2e (lane 3). The weak but specific band around 10 kDa in lane 2 represents the wild-type M2 protein whereas the larger band around 70 kDa represents the hlHA/M2e protein. Both bands are absent in the wild-type MVA control (lane 4).

The expression of the M1, NP and PB1 protein is detected with polyclonal guinea-pig anti-influenza H5N1 serum produced in house, a polyclonal goat antibody detecting the PB1 of Influenza A virus (Santa Cruz, Cat#: vC-19), and a monoclonal mouse-anti-NP-antibody (BioXcell, Cat# BE0159), respectively. The MVA-M1-VN and MVA-NP-VN induce expression of the M1 protein (around 27 kDa) and the NP protein (around 60 kDa) (not shown).

Example 3

Animal Experiments with the Single-Insert Vaccines

Protection Experiment

A standard protection experiment consists of two arms (primed with about $1\times10^3$-$1\times10^5$ TCID$_{50}$ H1N1v CA/07 and unprimed) of nine groups of mice each (respectively vaccinated i.m. with $1\times10^6$ pfu of the nine vaccines and controls shown in Table 2), a group consisting of six animals resulting in 108 animals, defines one set. The animals of one set are challenged with one of the six challenge viruses shown in Table 3 below.

TABLE 3

| Pre-treatment | Challenge strain | Subtype | Abbreviation |
| --- | --- | --- | --- |
| H1N1v/unprimed | A/California/07/2009 | H1N1 | CA/07 |
| H1N1v/unprimed | A/Vietnam/1203/2004 | H5N1 | VN/1203 |
| H1N1v/unprimed | A/HongKong/G9/ | H9N2 | HK/G9 |
| H1N1v/unprimed | A/Victoria/210/2009 | H3N2 | VI/09 |
| H1N1v/unprimed | A/FPV/Rostock/34 | H7N1 | RO/34 |
| H1N1v/unprimed | A/PR8/1934 | H1N1 | PR8 |

Female Balb/c mice are 8-10 weeks old at the pre-treatment time point and 14-16 weeks old at the time point of immunization with the vaccines and controls shown in Table 2. Mice were immunized intramuscularly twice (days 42 and 63) with $10^6$ pfu of the vaccines or wild type MVA, 3.75 µg whole virus preparation H9N2 A/HongKong/G9/1997 or with buffer (PBS). At day 84, mice were challenged intranasally with $10^3$ TCID$_{50}$ H5N1 A/Vietnam/1203/2004 (H5N1, CDC #2004706280), with $2.5\times10^4$ TCID$_{50}$ mouse adapted H9N2 A/HongKong/G9/1997 or with $1.66\times10^4$ TCID$_{50}$ H7N1 A/FPV/Rostock/34. The challenge doses correspond to approx. 30 LD50 for the H5N1 challenge and 32 LD50 for the H9N2 challenge per animal. Sera are collected at days 41, 62 and 85 and analyzed for HA-specific IgG concentration by HI titer or microneutralization assay.

The primary outcome of the animal experiments is protection as measured by lethal endpoint, weight loss, or lung titer. Further the ELISA titers of pooled pre-challenge sera measured against inactivated whole virus H5N1 strain A/Vietnam/1203/2004 are determined.

T Cell Experiments

Frequencies of influenza-specific CD4 and CD8 T cells are determined in immunized mice by flow cytometry. In a standard experiment, groups of 5 female BALB/c mice are immunized twice with the vaccines or controls listed in Table 2. Splenocytes are re-stimulated in-vitro using inactivated whole virus antigens of different influenza strains for CD4 T-cells and, when available, peptides representing the CD8 T-cell epitopes of the vaccine insert constructs and IFN-γ production are measured. All experiments are performed twice, using a total of 140 animals.

Other Experiments

An evaluation of the cell-mediated immunity after a single immunization, demonstration of functional activity of cytotoxic T-cells in a VITAL assay and assessment of recruitment of influenza-specific T-cells into the lungs of challenged animals are also carried out. The induction/expansion of vaccine-specific T-cells is also monitored in the primed mouse model by immunizing mice which resolved a influenza virus infection once with these vaccines.

Example 4

Construction and Characterization of Double-Insert rMVA Vectors

The following double-insert, rMVA and controls are utilized in the experiments described herein.

TABLE 4

| rMVA | Inserted influenza gene(s) | Comment |
|---|---|---|
| 1. MVA-hlHA-NP | headless HA + NP | Double insert construct |
| 2. MVA-hlHA/M2e-NP | headless HA/m2e fusion protein + NP | Double insert construct |
| 3. MVA-NP-VN | nucleoprotein | Control |
| 4. MVA-HA-VN | hemagglutinin | Control |
| 5. MVA-wt | empty vector | Neg. control |
| 6. PBS | — | Neg. control |

For the construction of the double insert rMVA vector co-expressing either the hlHA or hlHA/M2e gene cassette in combination with the NP protein gene cassette, the single insert MVA recombinants of Example 2 containing the hlHA or hlHA/M2e gene cassette are used. CEC cells were infected with MVA-hlHA or MVA-hlHA/Me2 and afterwards transfected with pd3-lacZ-mH5-NP-VN (see Example 2). Homologous recombination and propagation of the recombinant MVA vectors are performed as described in Example 2. The resulting double insert MVA vectors, named MVA-hlHA-NP or MVA-hlHA/M2e-NP, contain the hlHA or hlHA/M2e expression cassette in the D4R/D5R locus and the NP expression cassette in the del III locus. See FIG. 7.

The recombinant MVAs were characterized by Western Blot as described in Example 2. FIG. 8A shows the expression of the hlHA and hlHA/M2e after infection of CEC with MVA-hlHA-NP (lane 6) or MVA-hlHA/M2e-NP (lane 5). The bands around 40 kDa in lanes 3 and 6 represent the hlHA of the MVA-hlHA and MVA-hlHA-NP constructs. The band around 70 kDa in lane 5 represents the hlHA/M2e fusion protein. The HA bands are absent in the wild-type control in lane 4. The same samples were used for detection of NP protein expression in Western Blots (as described in Example 2). As shown in FIG. 8B, the recombinant MVAs MVA-hlHA-NP and MVA-hlHA/M2e-NP also induced expression of the NP protein in avian CEC cells. The bands around 60 kDa in lanes 2 to 4 represent the NP.

Example 5

Animal Experiments with the Double-Insert Vaccines or Vector Combinations

Protection Experiment

A standard experiment included eight groups of mice (vaccinated with the six vaccines and controls shown in Table 5) each group consisting of six animals. The protection experiments were carried out as described in Example 3. After challenge mice were monitored over a time period of 14 days and weight loss or symptoms including ruffled fur (score of 1), curved posture (score of 2), apathy (score of 3), and death (score of 4) were recorded. For ethical reasons, mice were euthanized after weight loss of >25%. Protection results are compiled in Table 5 and displayed in FIGS. 9 and 10.

TABLE 5

Protection of mice from death after double dose vaccinations with recombinant MVAs and homologous or heterologous challenge.

| | | After H5N1 VN1203[(1)] challenge | | After H9N2 HK/G9[(2)] challenge | |
|---|---|---|---|---|---|
| Gr. | Vaccine | Clinical score at day 14 | Protection n/nt[(3)] (%) | Clinical score at day 14 | Protection n/nt (%) |
| 1 | MVA-hlHA-NP | 2.83 | 2/6 (33) | 0 | 6/6 (100) |
| 2 | MVA-hlHA/M2e-NP | 1 | 5/6 (83) | 0 | 6/6 (100) |
| 3 | MVA-hlHA | 2.67 | 2/6 (33) | 3.33 | 1/6 (17) |
| 4 | MVA-hlHA/M2e | 4 | 0/6 (0) | 2.67 | 2/6 (33) |
| 5 | MVA-NP-VN | 3.33 | 2/6 (33) | 0 | 6/6 (100) |
| 6 | Homologous control vaccine[(4)] | 0 | 6/6 (100) | 0 | 6/6 (100) |
| 7 | MVA-wt[(5)] | 4 | 0/6 (0) | 2.83 | 2/6 (33) |
| 8 | PBS | 2.67 | 2/6 (33) | 4 | 0/6 (0) |

(1)VN1203, challenge strain A/Vietnam/1203/2004;
(2)HK/G9, challenge strain A/HongKong/G9/1997;
(3)n/nt, survival per group,
(4)Homologous control vaccine;
(5)wild-type MVA (NIH74 LVD clone 6).

As positive control mice were vaccinated with homologous control constructs. In case of H5N1 challenge mice were vaccinated with MVA-HA-VN (Hessel et al., 2011) and in case of H9N2 challenge mice were vaccinated with an inactivated whole virus preparation of the H9N2 A/HongKong/G9/1997 influenza virus. Both controls induced full protection (Table 5; FIGS. 9 and 10, panels E). In the wild-type MVA and buffer groups all mice showed marked weight loss compared to the positive control groups and nearly all mice died after challenge. Mice vaccinated with the single recombinant MVAs (MVA-hlHA, MVA-hlHA/M2e, MVA-D3-NP-VN) showed no significantly better protection after the strong H5N1 challenge compared to the negative control groups (FIG. 9 A-F). Also against heterosubtypic (H9N2) challenge no significant protection was seen in MVA-hlHA and MVA-hlHA/M2e vaccinated groups (FIG. 10).

Surprisingly, however, vaccination with the double construct expressing the fusion protein hlHA/M2e and the NP protein resulted in nearly full protection (FIG. 9 B, D, F) after the H5N1 challenge with approx. 30 LD50 per animal. Also after heterosubtypic challenge (with approx. 32 LD50 H9N2 virus) mice were fully protected after vaccination with the double recombinant MVA-hlHA/M2e-NP. Furthermore, the double recombinant MVA-hlHA-NP and the single recombinant MVA-NP-VN induced full protection against the heterosubtypic challenge with H9N2 (FIG. 10, B, D, F). As can be seen in the weight monitoring (FIGS. 9 and 10, panels B) and in the clinical scores (FIGS. 9 and 10, panels D), the double construct MVA-hlHA/M2e-NP showed the best results presumably by combined beneficial effects contributed by the different influenza antigens.

T Cell Experiments

Frequencies of influenza-specific CD4 and CD8 T cells are determined in immunized mice by flow cytometry. In a standard protocol experiment, groups of 5 female BALB/c mice are immunized twice with the vaccines or controls listed in Table 4. Splenocytes are re-stimulated in-vitro using inactivated whole virus antigens of different influenza strains for CD4 T-cells and, when available, peptides representing the CD8 T-cell epitopes of the vaccine insert constructs and IFN-γ production are measured. All experiments are performed twice.

Other Experiments

An evaluation of the cell mediated immunity after a single immunization, demonstration of functional activity of cytotoxic T-cells in a VITAL assay and assessment of recruitment of influenza-specific T-cells into the lungs of challenged animals are also carried out. The induction/expansion of vaccine-specific T-cells is also monitored in the primed mouse model by immunizing mice which resolved a influenza virus infection once with these vaccines.

Example 6

Construction and Characterization of Triple-Insert rMVA Vectors and Virus-Like Particles Influenza virus-like particles (VLPs) induce humoral and cellular responses and can protect against lethal challenges (Bright et al. 2007; Pushko et al. 2005; Song et al. 2010). VLPs chosen for experiments herein comprise either hlHA or hlHA/M2e in combination with NP and M1. The VLPs are generated from triple-insert MVA vectors.

For the construction of the triple-insert MVA vectors co-expressing either hlHA or hlHA/M2e in combination with the M1 (SEQ ID NO: 11) and the NP protein (SEQ ID NO: 13), the M1 gene (SEQ ID NO: 10) of pDD4-M1-VN is cloned downstream of the synthetic early/late promotor selP (Chakrabarti et al. 1997). The resulting gene cassette is cloned downstream of the hlHA or hlHA/M2e gene cassette in pDM-hlHA or pDM-hlHA/M2e. The resulting plasmids harboring a double gene cassette (pDM-hlHA-M1 and pDM-hlHA/M2e-M1) are used for recombination into defective MVA as described above. Afterwards, a recombination with an NP gene cassette (SEQ ID NO: 12)-containing plasmid (pD3-lacZ-gpt-NP-VN) is done resulting in a triple-insert MVA virus. This triple-insert MVA is plaque purified under transient marker selection.

The triple-insert MVA vectors, named MVA-hlHA-M1-NP or MVA-hlHA/M2e-M1-NP contain the hlHA or hlHA/M2e expression cassette and M1 expression cassette in tandem order in the D4R/D5R locus and the NP expression cassette in the del III locus (FIG. 7).

Detection of VLPs is as follows. HeLa or 293 cells are seeded into T175 $cm^2$ flasks and grown in DMEM+10% FCS+Pen/Strep. To generate VLPs, cells are infected with 1 MOI of single-insert MVA or triple-insert MVA recombinants, respectively. Empty MVA vectors or single-insert MVA recombinants without M1 are used as controls. At 1 h post infection (p.i.), the medium is replaced by DMEM+Pen/Strep and culture medium is harvested 48 h p.i. and cellular debris is pelleted by centrifugation at 2.000×g for 10 min. The procedure for analyzing VLPs by sucrose gradient density flotation and sucrose cushion has been described previously (Chen et al. 2007; Chen et al. 2005; Gomez-Puertes et al. 2000). The samples are then analyzed by immunoblotting. Additionally, electron microscopy (EM) analysis with medium of infected cells is performed.

Example 7

Animal Experiments with the Triple-Insert Vaccines or Vector Combinations

A standard experiment includes 6 groups of primed and unprimed mice (vaccinated with the 6 vaccines and controls shown in Table 5), each group consisting of 6 animals, resulting in 36 animals (1 set). The animals are challenged with one of the 6 challenge viruses shown in Table 3. In sum, there are 6 sets of 72 animals each requiring 432 mice to assess cross-protection in the primed and naive models.

TABLE 5

| rMVA | Inserted influenza gene(s) | comment |
|---|---|---|
| 1. MVA-hlHA-M1-NP | headless HA + nucleoprotein + matrix 1 | 3 inserts |
| 2. MVA-hlHA/M2e-M1-NP | headless HA/m2e fusion protein + nucleoprotein + matrix 1 | 3 inserts |
| 3. MVA-tbd | best construct from previous screening | control |
| 4. MVA-HA-VN | hemagglutinin | control |
| 5. MVA-wt | empty vector | neg. control |
| 6. PBS | — | neg. control |

The present invention is illustrated by the foregoing examples and variations thereof will be apparent to those skilled in the art. Therefore, no limitations other than those set out in the following claims should be placed on the invention.

All documents cited in this application are hereby incorporated by reference in their entirety for their disclosure described.

LITERATURE CITATIONS

Antoine, G., F. Scheiflinger, F. Dorner, and F. G. Falkner. 1998. The complete genomic sequence of the modified vaccinia Ankara strain: comparison with other orthopoxviruses. Virology 244:365-396.

Antoine, G., Scheiflinger, F., Holzer, G., Langmann, T., Falkner, F. G., and Dorner, F. 1996. Characterization of the vaccinia MVA hemagglutinin gene locus and its evaluation as an insertion site for foreign genes. Gene 177:43-46.

Assarsson, E., H. H. Bui, J. Sidney, Q. Zhang, J. Glenn, C. Oseroff, I. N. Mbawuike, J. Alexander, M. J. Newman, H. Grey, and A. Sette. 2008. Immunomic analysis of the repertoire of T-cell specificities for influenza A virus in humans. J Virol 82:12241-51.

Berthoud, T. K., M. Hamill, P. J. Lillie, L. Hwenda, K. A. Collins, K. J. Ewer, A. Milicic, H. C. Poyntz, T. Lambe, H. A. Fletcher, A. V. Hill, and S. C. Gilbert. 2011. Potent CD8+ T-cell immunogenicity in humans of a novel heterosubtypic influenza A vaccine, MVA-NP+M1. Clin Infect Dis 52:1-7.

Bommakanti, G., M. P. Citron, R. W. Hepler, C. Callahan, G. J. Heidecker, T. A. Najar, X. Lu, J. G. Joyce, J. W. Shiver, D. R. Casimiro, J. ter Meulen, X. Liang, and R. Varadarajan. 2010. Design of an HA2-based *Escherichia coli* expressed influenza immunogen that protects mice from pathogenic challenge. Proc Natl Acad Sci USA 107: 13701-6.

Bright, R. A., D. M. Carter, S. Daniluk, F. R. Toapanta, A. Ahmad, V. Gavrilov, M. Massare, P. Pushko, N. Mytle, T.

Rowe, G. Smith, and T. M. Ross. 2007. Influenza virus-like particles elicit broader immune responses than whole virion inactivated influenza virus or recombinant hemagglutinin. Vaccine 25:3871-8.

Brookes, R. H., Hill, P. C., Owiafe, P. K., Ibanga, H. B., Jeffries, D. J., Donkor, S. A., Fletcher, H. A., Hammond, A. S., Lienhardt, C., Adegbola, R. A., McShane, H., and Hill, A. V. 2008. Safety and immunogenicity of the candidate tuberculosis vaccine MVA85A in West Africa. PLoS One. 3:e2921.

Carroll, M. W., and B. Moss. 1997. Poxviruses as expression vectors. Curr Opin Biotechnol 8:573-7.

Cebere, I., Dorrell, L., McShane, H., Simmons, A., McCormack, S., Schmidt, C., Smith, C., Brooks, M., Roberts, J. E., Darwin, S. C., Fast, P. E., Conlon, C., Rowland-Jones, S., McMichael, A. J., and Hanke, T. 2006. Phase I clinical trial safety of DNA- and modified virus Ankara-vectored human immunodeficiency virus type 1 (HIV-1) vaccines administered alone and in a prime-boost regime to healthy HIV-1-uninfected volunteers. Vaccine 24:417-425.

Chakrabarti, S., J. R. Sisler, and B. Moss. 1997. Compact, synthetic, vaccinia virus early/late promoter for protein expression. Biotechniques 23:1094-7.

Chen, B. J., G. P. Leser, E. Morita, and R. A. Lamb. 2007. Influenza virus hemagglutinin and neuraminidase, but not the matrix protein, are required for assembly and budding of plasmid-derived virus-like particles. J. Virol. 81:7111-7123.

Chen, B. J., M. Takeda, and R. A. Lamb. 2005. Influenza virus hemagglutinin (H3 subtype) requires palmitoylation of its cytoplasmic tail for assembly: M1 proteins of two subtypes differ in their ability to support assembly. J Virol 79:13673-84.

Chen, J., S. A. Wharton, W. Weissenhorn, L. J. Calder, F. M. Hughson, J. J. Skehel, and D. C. Wiley. 1995. A soluble domain of the membrane-anchoring chain of influenza virus hemagglutinin (HA2) folds in *Escherichia coli* into the low-pH-induced conformation. Proc Natl Acad Sci USA 92:12205-9.

De Filette, M., W. Martens, K. Roose, T. Deroo, F. Vervalle, M. Bentahir, J. Vandekerckhove, W. Fiers, and X. Saelens. 2008. An influenza A vaccine based on tetrameric ectodomain of matrix protein 2. J Biol Chem 283:11382-7.

Denis, J., E. Acosta-Ramirez, Y. Zhao, M. E. Hamelin, I. Koukavica, M. Baz, Y. Abed, C. Savard, C. Pare, C. Lopez Macias, G. Boivin, and D. Leclerc. 2008. Development of a universal influenza A vaccine based on the M2e peptide fused to the papaya mosaic virus (PapMV) vaccine platform. Vaccine 26:3395-403.

Ekiert, D. C., G. Bhabha, M. A. Elsliger, R. H. Friesen, M. Jongeneelen, M. Throsby, J. Goudsmit, and I. A. Wilson. 2009. Antibody recognition of a highly conserved influenza virus epitope. Science 324:246-51.

Eliasson, D. G., K. El Bakkouri, K. Schon, A. Ramne, E. Festjens, B. Lowenadler, W. Fiers, X. Saelens, and N. Lycke. 2008. CTA1-M2e-DD: a novel mucosal adjuvant targeted influenza vaccine. Vaccine 26:1243-52.

Epstein, S. L. 2006. Prior H1N1 influenza infection and susceptibility of Cleveland Family Study participants during the H2N2 pandemic of 1957: an experiment of nature. J Infect Dis 193:49-53.

Fan, J., X. Liang, M. S. Horton, H. C. Perry, M. P. Citron, G. J. Heidecker, T. M. Fu, J. Joyce, C. T. Przysiecki, P. M. Keller, V. M. Garsky, R. Ionescu, Y. Rippeon, L. Shi, M. A. Chastain, J. H. Condra, M. E. Davies, J. Liao, E. A. Emini, and J. W. Shiver. 2004. Preclinical study of influenza virus A M2 peptide conjugate vaccines in mice, ferrets, and rhesus monkeys. Vaccine 22:2993-3003.

Gomez-Puertas, P., C. Albo, E. Perez-Pastrana, A. Vivo, and A. Portela. 2000. Influenza virus matrix protein is the major driving force in virus budding. J Virol 74:11538-47.

Graham, F. L., and A. J. van der Eb. 1973. A new technique for the assay of infectivity of human adenovirus 5 DNA. Virology 52:456-67.

Greenbaum, J. A., M. F. Kotturi, Y. Kim, C. Oseroff, K. Vaughan, N. Salimi, R. Vita, J. Ponomarenko, R. H. Scheuermann, A. Sette, and B. Peters. 2009. Pre-existing immunity against swine-origin H1N1 influenza viruses in the general human population. Proc Natl Acad Sci USA 106:20365-70.

Hessel, A., M. Schwendinger, D. Fritz, S. Coulibaly, G. W. Holzer, N. Sabarth, O. Kistner, W. Wodal, A. Kerschbaum, H. Savidis-Dacho, B. A. Crowe, T. R. Kreil, P. N. Barrett, and F. G. Falkner. 2010. A pandemic influenza H1N1 live vaccine based on modified vaccinia Ankara is highly immunogenic and protects mice in active and passive immunizations. PLoS One 5:e12217.

Hessel et al., 2011. PLoS ONE 6(1): e16247. doi:10.1371/journal.pone.0016247

Hoelscher, M. A., S. Garg, D. S. Bangari, J. A. Belser, X. Lu, I. Stephenson, R. A. Bright, J. M. Katz, S. K. Mittal, and S. Sambhara. 2006. Development of adenoviral-vector-based pandemic influenza vaccine against antigenically distinct human H5N1 strains in mice. Lancet 367:475-481.

Hoelscher, M. A., L. Jayashankar, S. Garg, V. Veguilla, X. Lu, N. Singh, J. M. Katz, S. K. Mittal, and S. Sambhara. 2007. New pre-pandemic influenza vaccines: an egg- and adjuvant-independent human adenoviral vector strategy induces long-lasting protective immune responses in mice. Clin. Pharmacol. Ther. 82:665-671.

Holzer, G. W., W. Gritschenberger, J. A. Mayrhofer, V. Wieser, F. Dorner, and F. G. Falkner. 1998. Dominant host range selection of vaccinia recombinants by rescue of an essential gene. Virology 249:160-6.

Kashyap, A. K., J. Steel, A. F. Oner, M. A. Dillon, R. E. Swale, K. M. Wall, K. J. Perry, A. Faynboym, M. Ilhan, M. Horowitz, L. Horowitz, P. Palese, R. R. Bhatt, and R. A. Lerner. 2008. Combinatorial antibody libraries from survivors of the Turkish H5N1 avian influenza outbreak reveal virus neutralization strategies. Proc Natl Acad Sci USA 105:5986-91.

Kreijtz, J. H., M. G. de, C. A. van Baalen, R. A. Fouchier, A. D. Osterhaus, and G. F. Rimmelzwaan. 2008. Cross-recognition of avian H5N1 influenza virus by human cytotoxic T-lymphocyte populations directed to human influenza A virus. J. Virol. 82:5161-5166.

Kreijtz, J. H., Y. Suezer, G. de Mutsert, G. van Amerongen, A. Schwantes, J. M. van den Brand, R. A. Fouchier, J. Lower, A. D. Osterhaus, G. Sutter, and G. F. Rimmelzwaan. 2009. MVA-based H5N1 vaccine affords cross-clade protection in mice against influenza A/H5N1 viruses at low doses and after single immunization. PLoS One 4:e7790.

Kreijtz, J. H., Y. Suezer, G. de Mutsert, J. M. van den Brand, G. van Amerongen, B. S. Schnierle, T. Kuiken, R. A. Fouchier, J. Lower, A. D. Osterhaus, G. Sutter, and G. F. Rimmelzwaan. 2009. Preclinical evaluation of a modified vaccinia virus Ankara (MVA)-based vaccine against influenza A/H5N1 viruses. Vaccine 27:6296-9.

Kreijtz, J. H., Y. Suezer, G. de Mutsert, J. M. van den Brand, G. van Amerongen, B. S. Schnierle, T. Kuiken, R. A. Fouchier, J. Lower, A. D. Osterhaus, G. Sutter, and G. F.

Rimmelzwaan. 2009. Recombinant modified vaccinia virus Ankara expressing the hemagglutinin gene confers protection against homologous and heterologous H5N1 influenza virus infections in macaques. J Infect Dis 199:405-13.

Kreijtz, J. H., Y. Suezer, G. van Amerongen, G. de Mutsert, B. S. Schnierle, J. M. Wood, T. Kuiken, R. A. Fouchier, J. Lower, A. D. Osterhaus, G. Sutter, and G. F. Rimmelzwaan. 2007. Recombinant modified vaccinia virus Ankara-based vaccine induces protective immunity in mice against infection with influenza virus H5N1. J. Infect. Dis. 195:1598-1606.

Lambert, L. C., and A. S. Fauci. 2010. Influenza Vaccines for the Future. N Engl J Med 363:2036-2044.

Lee, L. Y., L. A. Ha do, C. Simmons, J. M. D. de, N. V. Chau, R. Schumacher, Y. C. Peng, A. J. McMichael, J. J. Farrar, G. L. Smith, A. R. Townsend, B. A. Askonas, S. Rowland-Jones, and T. Dong. 2008. Memory T cells established by seasonal human influenza A infection cross-react with avian influenza A (H5N1) in healthy individuals. J. Clin. Invest 118:3478-3490.

Mackett, M., Smith, G. L., and Moss, B. 1982. Vaccinia virus: a selectable eukaryotic cloning and expression vector. Proc. Natl. Acad. Sci. U.S. A 79:7415-7419.

Mayrhofer, J., S. Coulibaly, A. Hessel, G. W. Holzer, M. Schwendinger, P. Bruhl, M. Gerencer, B. A. Crowe, S. Shuo, W. Hong, Y. J. Tan, B. Dietrich, N. Sabarth, H. Savidis-Dacho, O. Kistner, P. N. Barrett, and F. G. Falkner. 2009. Nonreplicating vaccinia virus vectors expressing the H5 influenza virus hemagglutinin produced in modified Vero cells induce robust protection. J Virol 83:5192-203.

McMichael, A. J., C. A. Michie, F. M. Gotch, G. L. Smith, and B. Moss. 1986. Recognition of influenza A virus nucleoprotein by human cytotoxic T lymphocytes. J Gen Virol 67 (Pt 4):719-26.

Meyer, H., Sutter, G., and Mayr, A. 1991. Mapping of deletions in the genome of the highly attenuated vaccinia virus MVA and their influence on virulence. J. Gen. Virol. 72 (Pt 5):1031-1038.

Moss, B., M. W. Carroll, L. S. Wyatt, J. R. Bennink, V. M. Hirsch, S. Goldstein, W. R. Elkins, T. R. Fuerst, J. D. Lifson, M. Piatak, N. P. Restifo, W. Overwijk, R. Chamberlain, S. A. Rosenberg, and G. Sutter. 1996. Host range restricted, non-replicating vaccinia virus vectors as vaccine candidates. Adv Exp Med Biol 397:7-13.

Neirynck, S., T. Deroo, X. Saelens, P. Vanlandschoot, W. M. Jou, and W. Fiers. 1999. A universal influenza A vaccine based on the extracellular domain of the M2 protein. Nat Med 5:1157-63.

Okuno, Y., Y. Isegawa, F. Sasao, and S. Ueda. 1993. A common neutralizing epitope conserved between the hemagglutinins of influenza A virus H1 and H2 strains. J Virol 67:2552-8.

Poon, L. L., Y. H. Leung, J. M. Nicholls, P. Y. Perera, J. H. Lichy, M. Yamamoto, T. A. Waldmann, J. S. Peiris, and L. P. Perera. 2009. Vaccinia virus-based multivalent H5N1 avian influenza vaccines adjuvanted with IL-15 confer sterile cross-clade protection in mice. J Immunol 182: 3063-71.

Price, G. E., M. R. Soboleski, C. Y. Lo, J. A. Misplon, C. Pappas, K. V. Houser, T. M. Tumpey, and S. L. Epstein. 2009. Vaccination focusing immunity on conserved antigens protects mice and ferrets against virulent H1N1 and H5N1 influenza A viruses. Vaccine 27:6512-21.

Price, G. E., M. R. Soboleski, C. Y. Lo, J. A. Misplon, M. R. Quirion, K. V. Houser, M. B. Pearce, C. Pappas, T. M. Tumpey, and S. L. Epstein. 2010. Single-dose mucosal immunization with a candidate universal influenza vaccine provides rapid protection from virulent H5N1, H3N2 and H1N1 viruses. PLoS One 5:e13162.

Pushko, P., T. M. Tumpey, F. Bu, J. Knell, R. Robinson, and G. Smith. 2005. Influenza virus-like particles comprised of the HA, NA, and M1 proteins of H9N2 influenza virus induce protective immune responses in BALB/c mice. Vaccine 23:5751-9.

Ricci et al., 2011. Virology Journal, 8:529.

Rimmelzwaan, G. F., and G. Sutter. 2009. Candidate influenza vaccines based on recombinant modified vaccinia virus Ankara. Expert Rev Vaccines 8:447-54.

Sanchez-Fauquier, A., N. Villanueva, and J. A. Melero. 1987. Isolation of cross-reactive, subtype-specific monoclonal antibodies against influenza virus HA1 and HA2 hemagglutinin subunits. Arch Virol 97:251-65.

Scheiflinger et al, 1998. Arch. Virol. 143, 467-474.

Schotsaert, M., M. De Filette, W. Fiers, and X. Saelens. 2009. Universal M2 ectodomain-based influenza A vaccines: preclinical and clinical developments. Expert Rev Vaccines 8:499-508.

Slavik, I., Ciampor, F., and Mayer, V. 1983. Optimalized conditions of tick-borne encephalitis virus production in vitro. Acta Virol. 27:97-104.

Smith, G. L., J. Z. Levin, P. Palese, and B. Moss. 1987. Synthesis and cellular location of the ten influenza polypeptides individually expressed by recombinant vaccinia viruses. Virology 160:336-45.

Song, J. M., J. Hossain, D. G. Yoo, A. S. Lipatov, C. T. Davis, F. S. Quan, L. M. Chen, R. J. Hogan, R. O. Donis, R. W. Compans, and S. M. Kang. 2010. Protective immunity against H5N1 influenza virus by a single dose vaccination with virus-like particles. Virology 405:165-75.

Steel, J., A. C. Lowen, T. Wang, M. Yondola, Q. Gao, K. Haye, A. Garcia-Sastre, and P. Palese. 2010. Influenza virus vaccine based on the conserved hemagglutinin stalk domain. MBio 1.

Sui, J., W. C. Hwang, S. Perez, G. Wei, D. Aird, L. M. Chen, E. Santelli, B. Stec, G. Cadwell, M. Ali, H. Wan, A. Murakami, A. Yammanuru, T. Han, N. J. Cox, L. A. Bankston, R. O. Donis, R. C. Liddington, and W. A. Marasco. 2009. Structural and functional bases for broad-spectrum neutralization of avian and human influenza A viruses. Nat Struct Mol Biol 16:265-73.

Throsby, M., E. van den Brink, M. Jongeneelen, L. L. Poon, P. Alard, L. Cornelissen, A. Bakker, F. Cox, E. van Deventer, Y. Guan, J. Cinatl, J. ter Meulen, I. Lasters, R. Carsetti, M. Peiris, J. de Kruif, and J. Goudsmit. 2008. Heterosubtypic neutralizing monoclonal antibodies cross-protective against H5N1 and H1N1 recovered from human IgM+ memory B cells. PLoS One 3:e3942.

Tykodi, S. S, and Thompson, J. A. 2008. Development of modified vaccinia Ankara-5T4 as specific immunotherapy for advanced human cancer. Expert. Opin. Biol. Ther 8:1947-1953.

Ulmer, J. B., J. J. Donnelly, S. E. Parker, G. H. Rhodes, P. L. Felgner, V. J. Dwarki, S. H. Gromkowski, R. R. Deck, C. M. DeWitt, A. Friedman, and et al. 1993. Heterologous protection against influenza by injection of DNA encoding a viral protein. Science 259:1745-9.

Wyatt, L. S., S. T. Shors, B. R. Murphy, and B. Moss. 1996. Development of a replication-deficient recombinant vaccinia virus vaccine effective against parainfluenza virus 3 infection in an animal model. Vaccine 14:1451-8.

Yewdell, J. W., J. R. Bennink, G. L. Smith, and B. Moss. 1985. Influenza A virus nucleoprotein is a major target antigen for cross-reactive anti-influenza A virus cytotoxic T lymphocytes. Proc Natl Acad Sci USA 82:1785-9.

Zhao, G., Y. Lin, L. Du, J. Guan, S. Sun, H. Sui, Z. Kou, C. C. Chan, Y. Guo, S. Jiang, B. J. Zheng, and Y. Zhou. 2010. An M2e-based multiple antigenic peptide vaccine protects mice from lethal challenge with divergent H5N1 influenza viruses. Virol J 7:9.

Zhao, G., S. Sun, L. Du, W. Xiao, Z. Ru, Z. Kou, Y. Guo, H. Yu, S. Jiang, Y. Lone, B. J. Zheng, and Y. Zhou. 2010a. An H5N1 M2e-based multiple antigenic peptide vaccine confers heterosubtypic protection from lethal infection with pandemic 2009 H1N1 virus. Virol J 7:151.

Zhou, D., T. L. Wu, M. O. Lasaro, B. P. Latimer, E. M. Parzych, A. Bian, Y. Li, H. Li, J. Erikson, Z. Xiang, and H. C. Ertl. 2010b. A universal influenza a vaccine based on adenovirus expressing matrix-2 ectodomain and nucleoprotein protects mice from lethal challenge. Mol Ther 18:2182-9.

We claim:

1. A recombinant modified vaccinia virus Ankara (rMVA) comprising a first gene cassette encoding an influenza A headless hemagglutinin (hlHA) polypeptide of SEQ ID NO: 15 and a second gene cassette encoding influenza A nucleoprotein (NP).

2. A pharmaceutical composition comprising the rMVA of claim 1.

3. A method of inducing a heterosubtypic immune response to influenza A viruses in an individual comprising administering a pharmaceutical composition comprising the rMVA of claim 1 to the individual.

* * * * *

UNITED STATES PATENT AND TRADEMARK OFFICE
CERTIFICATE OF CORRECTION

PATENT NO. : 9,463,237 B2  
APPLICATION NO. : 13/982524  
DATED : October 11, 2016  
INVENTOR(S) : Falkner et al.

Page 1 of 1

It is certified that error appears in the above-identified patent and that said Letters Patent is hereby corrected as shown below:

On the Title Page

At (73) Assignee reads:  
BAXALTA INCORPORATED (Bannockburn, IL, US)  
BAXALTA GMBH (Glattpark (Opfikon) CH)

Should read:  
NANOTHERAPEUTICS, INC. (Alachua, FL)

Signed and Sealed this  
Twenty-eighth Day of March, 2017

Michelle K. Lee  
*Director of the United States Patent and Trademark Office*